(12) United States Patent
Nakaya

(10) Patent No.: US 10,448,913 B2
(45) Date of Patent: Oct. 22, 2019

(54) X-RAY IMAGING APPARATUS

(71) Applicant: SHIMADZU CORPORATION, Nakagyo-Ku, Kyoto-Shi, Kyoto (JP)

(72) Inventor: Tomohiro Nakaya, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 235 days.

(21) Appl. No.: 15/515,796

(22) PCT Filed: Oct. 3, 2014

(86) PCT No.: PCT/JP2014/076622
§ 371 (c)(1),
(2) Date: Dec. 21, 2017

(87) PCT Pub. No.: WO2016/051603
PCT Pub. Date: Apr. 7, 2016

(65) Prior Publication Data
US 2019/0142356 A1     May 16, 2019

(51) Int. Cl.
*A61B 6/02*     (2006.01)
*G01N 23/223*     (2006.01)
(Continued)

(52) U.S. Cl.
CPC .............. *A61B 6/487* (2013.01); *A61B 6/00* (2013.01); *A61B 6/505* (2013.01); *A61B 6/52* (2013.01); *A61B 5/4509* (2013.01); *A61B 6/10* (2013.01)

(58) Field of Classification Search
CPC ........... A61B 6/025; A61B 6/032; A61B 6/06; A61B 6/5205; A61B 6/5241;
(Continued)

(56) References Cited

U.S. PATENT DOCUMENTS

| 6,795,526 B2 * | 9/2004 | Kump | A61B 6/00 378/116 |
| 2013/0148779 A1 * | 6/2013 | Notohara | A61B 6/025 378/22 |

(Continued)

FOREIGN PATENT DOCUMENTS

| JP | 61-52860 | 3/1986 |
| JP | 2003-284708 | 10/2003 |

(Continued)

OTHER PUBLICATIONS

PCT/JP2014/076622, ISR and Written Opinion, dated Nov. 11, 2014, 7 pages—Japanese; 2 pages—English.

*Primary Examiner* — Irakli Kiknadze
(74) *Attorney, Agent, or Firm* — Andrew F. Young, Esq.; Lackenbach Siegel, LLP

(57) ABSTRACT

An X-ray imaging apparatus provides for an improvement of the imaging location of a pre-image P that is corrected based on a correction level calculated by a correction level calculation element 29. The correction level is calculated based on a distance between a center Ko of a vertebral area extracted from a pre-image P by a feature area extraction element 27 and a center Po of the pre-image P. Once the pre-image is generated, the pre-image is corrected so that the center Ko of the vertebral area coincides with the center Po of the pre-image P. The pre-image is generated by irradiating a pulse X-ray once from an X-ray tube 5 by pushing down a pre-image generation directive button 33a. Regardless the length of pushing-down time, a X-ray irradiation time is always a predetermined short time, so that an X-ray irradiation time can be an absolutely predetermined short time by a simplified operation. As results, when the imaging range of the mensurative X-ray image is set, the X-ray irradiation time is reduced and a radiation dose is sup- (Continued)

pressed. Also, the imaging range correction of the pre-image P can be quickly corrected, so that time needed for imaging the image is shortened.

11 Claims, 16 Drawing Sheets

(51) Int. Cl.
*A61B 6/00* (2006.01)
*A61B 5/00* (2006.01)
*A61B 6/10* (2006.01)

(58) Field of Classification Search
CPC ..... A61B 6/4452; A61B 6/4476; A61B 6/466; A61B 6/502; A61B 6/542; A61B 6/547; A61B 6/4233; A61B 6/487; A61B 6/02; A61B 6/027; A61B 6/00; A61B 6/488; A61B 6/544; A61B 5/4509; A61B 6/10; A61B 6/505; A61B 6/52; G06T 2207/10116; G06T 2207/10144; G06T 2207/20021; G06T 2207/20104; G06T 2207/30004; G06T 7/11

USPC ............. 378/42, 50, 98.9, 116, 95, 108
See application file for complete search history.

(56) References Cited

U.S. PATENT DOCUMENTS

| 2014/0198896 A1* | 7/2014 | Hemmendorff ...... A61B 6/4452 378/37 |
| 2017/0135658 A1* | 5/2017 | Saito ..................... A61B 6/06 |

FOREIGN PATENT DOCUMENTS

| JP | 2007-195612 | 8/2007 |
| JP | 2007-222500 | 9/2007 |
| JP | 2013-184017 | 9/2013 |
| JP | 2014-138837 | 7/2014 |

* cited by examiner (a)

(b)

(a)

(b)

(a)

(b)

(c)

X-RAY IMAGING APPARATUS

CROSS REFERENCE TO RELATED APPLICATIONS

This application relates to, and claims priority from Ser. No.: PCT/JP2014/076622 filed Oct. 3, 2014, the entire contents of which are incorporated herein by reference.

FIGURE SELECTED FOR PUBLICATION

FIGS. 8(A). 8(B)

BACKGROUND OF THE INVENTION

Field of the Invention

The present invention relates to an X-ray imaging apparatus that performs a bone densitometry using an X-ray and particularly relates to a technology that corrects an imaging location (position) of the X-ray image (radiograph) and an X-ray irradiation field.

Description of the Related Art

Bone densitometry for data to diagnose an osteoporosis and so forth may be carried out in a medical practice. One example of the bone densitometry methods is a method of taking an X-ray image (radiograph) relative to lumbar vertebrae using an X-ray imaging apparatus. And the dual energy subtraction method is disclosed as a method of taking an X-ray image for the bone densitometry (mensurative X-ray image).

The dual energy subtraction method is a method to generate a subtracted image (subtraction image) by performing an (subtraction) image processing on subtracting the low-voltage X-ray image obtained by irradiating a low-energy X-ray to a subject from the high-voltage X-ray image obtained by irradiating a high-energy X-ray to the subject. In such case, an image of the less radiolucent bone tissue and an image of the more radiolucent soft tissue can be obtained individually.

In addition, when a mensurative X-ray image is imaged, a method by which an X-ray radiation field is adjusted to be like a slit (strip shape) and the X-ray radiation is executed so that an incident of scattering of X-rays and deformation of the X-ray image and so forth can be prevented is disclosed (e.g., Patent Document 1). Specifically, while both the X-ray tube and the collimator that adjusts the X-ray radiation field so as to be a trip shape are being moved in parallel (translated) along the body axis direction of the subject, the X-ray radiation is repeated, so that multiple strip-shaped subtraction images can be generated. Then each generated subtraction image is continuously connected along the body axis direction of the subject, so that a mensurative X-ray image extending along the body axis direction of the subject can be reconstructed. An operator then analyzes a bone density using the reconstructed mensurative X-ray image.

The inventor sets forth an X-ray imaging apparatus that is applied to such bone densitometry. Referring to FIG. 15A, a conventional X-ray imaging apparatus 100 comprises a tabletop 101 on which a subject M is loaded, an X-ray tube 103 that irradiates an X-ray to the subject M, and an X-ray detector 105 that detects and converts the X-ray to an X-ray detection signal as an electric signal. An output from the X-ray irradiated from the X-ray tube 103 is controlled by the X-ray irradiation control element, not shown in FIG.

A collimator 107 is installed under the X-ray tube 103. The collimator 107 limits X-rays irradiated from the X-ray tube 103 to a pyramid-like cone shape according to the control by the collimator control mechanism 109. The X-ray tube 103 and the X-ray detector 105 constitutes an imaging system and are in-place facing each other sandwiching the tabletop 101. A flat panel detector (FPD) and so forth can be used as the X-ray detector 105. Each element of the imaging system is movable in the x-direction (longitudinal direction of the tabletop 101) and the body axis direction of the subject M. Movement of each element of the imaging system is controlled by the imaging system movement mechanism 111.

An image generation element 113 is installed in the posterior of the X-ray detector 105. The image generation element 113 generates a high-voltage X-ray image and a low-voltage image based on the X-ray detection signal output from the X-ray detector 105. A subtraction processing element 115 executes a subtraction processing in which the low-voltage X-ray image is subtracted from the high-voltage X-ray image generated by the image generation element 113 and generates multiple subtraction images. Then, a reconstruction element 117 connects each generated subtraction image generated by the subtraction processing element 115 along the body axis direction of the subject M so that a mensurative X-ray image applicable to the bone densitometry can be reconstructed.

When the mensurative X-ray image applied to the bone densitometry is taken, the imaging location of the mensurative X-ray image is set in advance. Specifically, an X-ray fluoroscopy that irradiate a low-dose X-ray to the subject M under the condition in which the X-ray irradiation field is broad is performed so as to refer the X-ray image incorporated in the mensurative X-ray image. An X-ray fluoroscopic image P (pre-image P) showing a vertebra K and a pelvis L of the lumber vertebra of the subject M are taken intermittently by the X-ray fluoroscopy. The pre-image P is an X-ray image that is applied to set the imaging range of the mensurative X-ray image.

An operator controls the location of the X-ray tube 103 adequately referring to the X-ray image in the obtained pre-image P while performing the X-ray fluoroscopy, and adjust the imaging location of the pre-image P so as to bring the vertebra K, i.e., a target, in the center of the pre-image P (referring to FIG. 15B). Each vertebra K of the lumber vertebra of the subject M is displayed on the centerline H in the y-direction relative to the pre-image P for which the imaging location is adjusted (referring to FIG. 15C). And the imaging range of the pre-image P for which the imaging location is adjusted is set as an imaging range of the mensurative X-ray image. The X-ray irradiation field subsequently is limited to a strip shape broadening in the y-direction and having a thickness T in the x-direction based on the imaging range of the pre-image P, and the X-ray tube 103 shifts to the location indicated by the solid line in FIG. 16A Referring to FIG. 16A, while the X-ray tube 103 is subsequently shifting from the location indicated by the solid line to the location indicated by the broken line, an X-ray imaging is performed. At this time, a high-voltage and a low-voltage are alternately added to the X-ray tube 3 that irradiates X-rays every time when the X-ray tube 103 shifts in the distance corresponding to the thickness T in the x-direction. The image generation element 113 generates each high-voltage X-ray image and low-voltage X-ray image at the perspective imaging locations in accordance with each voltage. The subtraction processing element 115 generates a subtraction image based on each X-ray image.

Accordingly, the strip-shaped subtraction images S1-S6 having T that is the width in the x-direction are generated relative to the image range of the pre-image P (FIG. 16B, upper portion). At end, the reconstruction element 117 connects the subtraction images S1 to S6 each other in the x-direction and reconstructs an mensurative X-ray image Q showing the vertebra K and the pelvis L and so forth of the lumber vertebra (FIG. 16B, lower portion).

The X-ray irradiated when each subtraction image S1☐S6 is generated has a little broadening in the x-direction. Therefore, each subtraction image S1 to S6 has less effect due to an X-ray scattering and a little deformation of the X-ray image. Accordingly, the mensurative X-ray image Q obtained by reconstructing such images is a high-quality X-ray image suitable for an analysis of bone density.

RELATED PRIOR ART DOCUMENTS

Patent Document

Patent Document 1
JP 2013-184017 A1

ASPECTS AND SUMMARY OF THE INVENTION

Objects To Be Solved

Nevertheless, in the case of a conventional example having such structure, following problems are remained to be solved.

Specifically, when the imaging location for the pre-image P is adjusted according to a conventional apparatus, the fine adjustment of the location of the X-ray tube 103 must be performed while generating X-ray fluoroscopic images intermittently until the imaging location for the pre-image P becomes a suitable location. In such case, the X-ray is continuously irradiated to the subject M until the X-ray tube 103 shifts to the suitable location, so that the radiation dose to the subject M increases on the X-ray fluoroscopy.

In addition, it is desirable that the imaging range of the pre-image P is broad so that the accurate imaging range of the mensurative X-ray image Q can be assured more absolutely. On the other hand, a required region for bone densitometry relative to the mensurative X-ray image Q is limited to the region of the bone tissue such as the vertebra K of the lumber vertebra and the periphery of the bone tissue. However, the X-ray irradiation field of the subtraction images S☐S6 is broad in the y-direction, so that the conventional mensurative X-ray image Q includes an unexpected region against the bone density analysis (e.g., the region indicated by the reference sign R). Accordingly, the X-ray is irradiated to the unexpected region against the bone densitometry, it is concerned that the X-ray dose to the subject M on the X-ray imaging must increase.

Considering such circumstances, the object of the present invention is to provide an X-ray imaging device capable of acquiring a long-length image naturally connected.

Means For Solving The Problem

The present invention constitutes the following structure to solve such problem.

Specifically, an X-ray imaging apparatus of the present invention comprises: an X-ray source that irradiates an X-ray to a subject; a detection means that detects the X-ray transmitted through the subject; an imaging system shifting means that shifts the imaging system relative to the subject and further comprises the X-ray source and the X-ray detection means; a strip image generation means that generate a plurality of strip images that are X-ray images having a strip shape, of which the short direction is the body axis direction of the subject, along the body axis of the subject by using the detection signal output from the X-ray detection means; a reconstruction means that reconstructs a single combined image by connecting the plurality of the strip images, which are generated by the strip image generation means, along the body axis direction of the subject: a pre-image generation means that generates an initial X-ray image as the pre-image, which is applied to set the imaging range of the combined image by using the using the detection signal output from the X-ray detection means; a pre-image generation directive means that inputs a directive for generation of the pre-image; an irradiation control means that controls the X-ray source so as to make a single irradiation of a pulse X-ray from the X-ray source based on the directive input to the pre-image generation directive means; a feature area extraction means that extracts a feature area from the initial X-ray imaged shown in the pre-image; a correction level calculation means that calculates a locational relationship between the center of the feature area extracted by the feature area extraction means and the center of the pre-image as a correction level; an imaging system shifting control means that controls the imaging system shifting means so that the center of the feature area coincides with the center of the combined image based on the correction level calculated by the correction level calculation mean.

An X-ray imaging apparatus according to the present invention, wherein the feature area extraction means extracts a feature area from the pre-image applied to set the imaging range of the combined image. The correction level calculation means calculates a correction level based on the locational relationship between the center of the feature area extracted from the X-ray image of the pre-image and the center of the pre-image. The imaging system shifting control means controls the imaging system shifting means based on the correction level. Specifically, once the pre-image is generated, the extraction of the feature area and the calculation of the correction level are automatically executed.

And the imaging system shifting control means controls the imaging system shifting means so that the center of the feature area coincides with the center of the imaging range of the combined image, and shifts the respective imaging systems. The correction level is a value calculated based on the locational relationship between the center of the feature area extracted from the X-ray image of the pre-image and the center of the pre-image. Accordingly, once one pre-image is generated, a suitable location of the imaging system is automatically calculated so that the center of the feature area can coincide with the center of the pre-image.

Accordingly, it is unnecessary that the pre-image is generated intermittently by continuously irradiating X-rays so that the location of the imaging system can be set as the center of the feature area coincides with the center of the pre-image. In addition, the suitable imaging range of the combined image can be set quickly by generating the pre-image so that the center of the feature area can coincide with the center of the pre-image. As results, the irradiation time of the X-ray becomes short, so that the radiation dose to the subject can be suppressed as low. Further, the imaging range of the combined image can be set quickly, so that the time duration needed to take the combined image can be shortened.

Further, the pre-image can be generated by inputting the directive to the pre-image generation directive means. And the irradiation makes a single irradiation of a pulse X-ray from the X-ray source based on the directive input to the pre-image generation directive means; In such case, regardless the difference in-between the input-time of the pre-image generation directive means, the X-ray irradiation time is always short as predetermined corresponding to the single irradiation of the pulse X-ray. Therefore, the x-ray irradiation time is absolutely shortened as predetermined by such simple operation. As results, it is absolutely avoidable that the X-ray irradiation time is different from the generated pre-image to the other, in addition to a suppressible radiation dose to the subject M.

In addition, the X-ray imaging apparatus of the present invention, wherein it is preferable that the imaging system shifting control means controls the imaging system shifting means so that the center of the feature area coincides with the center of the imaging range of the pre-image, and the pre-image generation means regenerates the pre-image following the control of the imaging system shifting means by the imaging system shifting control means so that the center of the feature area coincides with the center of the imaging range of the pre-image.

According to the X-ray imaging apparatus of the present invention, the pre-image generation means regenerates the pre-image following the imaging system shifting control means controls the imaging system shifting means so that the center of the feature area coincides with the center of the imaging range of the pre-image. In such case, the center of the regenerated pre-image coincides with the center of the feature area and coincides with the center of the combined image at the same time. Accordingly, whether the center of the combined image actually coincides with the center of the feature area or not can be made sure in advance by referring to the regenerated pre-image. Therefore, the imaging range of the combined image can be set in the more suitable location.

In addition, the X-ray imaging apparatus of the present invention, wherein it is preferable that the imaging system shifting control means controls the imaging system shifting means so that the center of the feature area coincides with the center of the imaging range of the combined image, and shifts the imaging system from the imaging location of the pre-image to the imaging location of the strip image.

According to the X-ray imaging apparatus of the present invention, the imaging system shifting control means shifts the imaging system from the imaging location of the pre-image to the imaging location of the strip image. In such case, the imaging system directly shifts from the imaging location of the pre-image to the imaging location of the strip image based on the correction level following the pre-image is generated, and then initiates imaging the strip image. Accordingly, the time needed for imaging the combined image can be shortened, so that the burden to the operator and the patient can decrease. In addition, the combined image can be imaged more efficiently.

In addition, it is preferable that the X-ray imaging apparatus of the present invention comprises: a collimator, having a diaphragm that shields the X-ray, that controls the irradiation field of the X-ray irradiated from the X-ray source; a collimator control means that controls opening-and-closing and shifting of the diaphragm; and an aperture calculation element that calculates the aperture of the diaphragm as the aperture based on the width of the feature area extracted by the feature area extraction means when each strip image is generated; and wherein the respective strip images are generated by that the collimator control means controls the opening-and-closing shift of the diaphragm based on each aperture.

According to the X-ray imaging apparatus of the present invention, the aperture calculation element calculates the aperture based on the width of the feature area extracted from the X-ray image incorporated in the pre-image. The aperture is an aperture of the diaphragm when the respective strip images are generated and a suitable aperture is calculated based on the width of the feature area relative to the respective strip images.

And the respective strip images are generated by that the collimator control means controls the opening-and-closing and shifting of the diaphragm based on each aperture. Therefore, the respective strip images are generated by irradiation of the X-ray to the suitable irradiation field set based on the feature area. Accordingly, the range in which X-rays are irradiated when each strip image is generated can be adequately controlled, so that the radiation dose to the subject can be suppressed lesser.

In addition, it is preferable that the X-ray imaging apparatus of the present invention comprises: a subtraction processing means that performs on the strip image generated by the strip image generation means when a high-voltage is added to the X-ray source and the strip image generated by the strip image generation means when a low-voltage is added to the X-ray source.

An X-ray imaging apparatus according to the present invention, wherein a subtraction processing means performs on the strip image generated by the strip image generation means when the high-voltage is added to the X-ray source and the strip image generated by the strip image generation means when the low-voltage is added to the X-ray source. The images of the area having a different transmittance of the X-ray can be obtained individually by the subtraction processing. And the reconstruction means connects the trips images on which the subtraction processing is performed and reconstructs the combined image. In such case, the subtraction processing is performed on any image incorporated in the combined image. Accordingly, a highly accurate diagnosis (examination) can be carried out relative to the broad target area by applying the combined image.

In addition, it is preferable that the X-ray imaging apparatus of the present invention comprises: a subtraction processing means that performs on the combine image reconstructed by the reconstruction means when a high-voltage is added to the X-ray source and the combined image reconstructed by the reconstruction means when a low-voltage is added to the X-ray source.

According to the X-ray imaging apparatus of the present invention, the subtraction processing means performs a subtraction processing on the combined image reconstructed when the high-voltage is added to the X-ray source and the combined image reconstructed when the low-voltage is added to the X-ray source. In such case, the images of the area having a different transmittance of the X-ray in the broad area can be obtained individually by the subtraction processing. Accordingly, a highly accurate diagnosis (examination) can be carried out relative to the broader target area by applying the combined image on the subtraction processing is performed.

In addition, according to the X-ray imaging apparatus of the present invention, it is preferable that the feature area extracted by the feature area extraction means is a vertebral area of the subject.

According to the X-ray imaging apparatus of the present invention, the feature area extraction means extracts the vertebral area of the subject from the X-ray image of the pre-image. And the pre-image correction means corrects the pre-image so that the center of the vertebral area coincides with the center of the pre-image. In such case, the combined image obtained by using the corrected pre-image is the image adequately incorporating the vertebral area. The vertebral area is the region applied to the bone densitometry and so forth, so that the bone densitometry can be adequately performed by using the combined image.

In addition, according to the X-ray imaging apparatus of the present invention, it is preferable that the aperture calculation means calculates the aperture relative to the respective strip images so that the region required for measurement of the bone density in which the distance from the vertebral area is shorter than a predetermined value and the region of the vertebra can be included in the X-ray irradiation field.

According to the X-ray imaging apparatus of the present invention, the aperture calculation means calculates the aperture so that the region required for measurement of the bone density in which the distance from the vertebral area is shorter than a predetermined value and the region of the vertebra can be included in the X-ray irradiation field. Accordingly, the range of the X-ray irradiation field in which the bone densitometry is feasible can be determined while suppressing the radiation dose to the subject based on the aperture. In addition, the aperture is calculated for each strip image, so that the range of the X-ray irradiation field in which the bone densitometry is feasible can be determined while suppressing the radiation dose to the subject relative to each strip image Accordingly, while suppressing the radiation dose to the subject, the combined image suitable for the bone densitometry can be obtained.

In addition, the X-ray imaging apparatus of the present invention, wherein it is preferable that the correction level calculation means calculates the correction level referring to the pre-image generated that is generated relative to the same subject in the past.

According to the X-ray imaging apparatus of the present invention, the correction level is calculated referring the pre-imaged of the same subject generated in the past. In such case, the correction level is calculated referring the range of the feature area extracted from the past pre-image and so forth. As results, the more accurate correction level can be calculated corresponding to the feature of the subject, so that the more adequate combined image for diagnosis (examination) can be obtained.

In addition, it is preferable that the X-ray imaging apparatus of the present invention comprises: a display means that displays the pre-image generated by the pre-image generation means: and a correction means that corrects the range of the extracted feature area relative to the pre-image that the display means displays.

The X-ray imaging apparatus according to the present invention comprises the correction means that corrects the range of the extracted feature area relative to the pre-image that the display means displays. In such case, the operator corrects as needed the range of the feature area that the feature area extraction means extracts from the pre-image to be a more appropriate range referring the displayed pre-image. The correction level is calculated corresponding to the location of the center of the feature area so that the more accurate correction level can be calculated by the correction of the range of the feature area. As results, the combined image that allows the more accurate examination can be obtained.

The present invention can constitute the following structure to achieve such purpose.

Specifically, an X-ray imaging apparatus of the present invention comprises: an X-ray source that irradiates an X-ray to a subject; a detection means that detects the X-ray transmitted through the subject: an imaging system shifting means that shifts the imaging system relative to the subject and which further comprising the X-ray source and the X-ray detection mean; a pre-image generation means that generates an initial X-ray image as the pre-image, which is applied to set the imaging range of the target area of the subject by using the using the detection signal output from the X-ray detection means; a pre-image generation directive means that inputs a directive for generation of the pre-image; an irradiation control means that controls the X-ray source to make a single irradiation of a pulse X-ray from the X-ray source based on the directive input to the pre-image generation directive means; a feature area extraction means that extracts a feature area from the initial X-ray image incorporated in the pre-image; a correction level calculation means that calculates a locational relationship between the center of the feature area extracted by the feature area extraction means and the center of the pre-image as a correction level; an imaging system shifting control means that controls the imaging system shifting means so that the center of the feature area coincides with the center of the target area based on the correction level calculated by the correction level calculation mean.

According to the X-ray imaging apparatus of the present invention, the feature area extraction means extracts the feature area from the pre-image applied to set the imaging ranged relative to the target area of the subject. The correction level calculation means calculates the correction level based on the locational relationship between the center of the feature area extracted from the X-ray image of the pre-image and the center of the pre-image. The imaging system shifting control means controls the imaging system shifting means based on the correction level. Specifically, once the pre-image is generated, the extraction of the feature area and the calculation of the correction level are automatically executed.

And the imaging system shifting control means controls the imaging system shifting means so that the center of the feature area coincides with the center of the imaging range of the target area, and shifts the respective imaging systems. The correction level is a value calculated based on the locational relationship between the center of the feature area extracted from the X-ray image of the pre-image and the center of the pre-image. Accordingly, once one pre-image is generated, a suitable location of the imaging system is automatically calculated so that the center of the feature area can coincide with the center of the imaging range relative the target area.

Accordingly, it is unnecessary that the pre-image is generated intermittently by continuously irradiating X-rays so that the location of the imaging system can be set as the center of the feature area coincides with the center of the imaging range relative to the target area. In addition, the suitable imaging range of the target area can be set quickly by generating one pre-image so that the center of the feature area can coincide with the center of the imaging range relative to the target area. As results, the irradiation time of the X-ray becomes short, so that the radiation dose to the subject can be suppressed as low. Further, the imaging range of the target area can be set quickly, so that time needed to take the target area can be shortened.

Further, the pre-image can be generated by inputting the directive to the pre-image generation directive means. And the irradiation makes a single irradiation of a pulse X-ray from the X-ray source based on the directive input to the pre-image generation directive means: In such case, regardless the difference in-between the input-time of the pre-image generation directive means, the X-ray irradiation time is always short as is predetermined corresponding to the single irradiation of the pulse X-ray. Therefore, the x-ray irradiation time is absolutely shortened as is predetermined by such simple operation. As results, it is absolutely avoidable that the X-ray irradiation time is different from one generated pre-image to the other, in addition to a suppressible radiation dose to the subject M.

EFFECT OF THE INVENTION

According to the X-ray imaging apparatus of the present invention, the feature area extraction means extracts the feature area from the pre-image applied to set the imaging range of the combined image. The correction level calculation means calculates the correction level based on the locational relationship between the center of the feature area extracted from the X-ray image of the pre-image and the center of the pre-image. The imaging system shifting control means controls the imaging system shifting means based on the correction level. Specifically, once the pre-image is generated, the extraction of the feature area and the calculation of the correction level are automatically executed.

And the imaging system shifting control means controls the imaging system shifting means so that the center of the feature area coincides with the center of the imaging range of the combined image, and shifts the respective imaging systems. The correction level is a value calculated based on the locational relationship between the center of the feature area extracted from the X-ray image of the pre-image and the center of the pre-image. Accordingly, once one pre-image is generated, a suitable location of the imaging system is automatically calculated so that the center of the feature area can coincide with the center of the combined image.

Accordingly, it is unnecessary that the pre-image is generated intermittently by continuously irradiating X-rays so that the location of the imaging system can be set as the center of the feature area coincides with the center of the combined image. In addition, the suitable imaging range of the combined image can be set quickly by generating one pre-image so that the center of the feature area can coincide with the center of the combined image. As results, the irradiation time of the X-ray becomes short, so that the radiation dose to the subject can be suppressed as low. Further, the imaging range of the combined image can be set quickly, so that the time duration needed to take the combined image can be shortened.

Further, the pre-image can be generated by inputting the directive to the pre-image generation directive means. And the irradiation makes a single irradiation of a pulse X-ray from the X-ray source based on the directive input to the pre-image generation directive means. In such case, regardless the difference in-between the input-time of the pre-image generation directive means, the X-ray irradiation time is always short as predetermined corresponding to the single irradiation of the pulse X-ray. Therefore, the x-ray irradiation time is absolutely short as is predetermined by such simple operation. As results, it is absolutely avoidable that the X-ray irradiation time is different from one generated pre-image to the other, in addition to a suppressible radiation dose to the subject M.

The above and other aspects, features and advantages of the present invention will become apparent from the following description read in conjunction with the accompanying drawings, in which like reference numerals designate the same elements.

BRIEF DESCRIPTION OF THE DRAWINGS

FIG. 2A is the cross-section view illustrating the collimator according to the aspect of the Embodiment 1 facing the y-direction.

FIG. 2B is a cross section view illustrating the collimator according to the aspect of the Embodiment 1 facing the x-direction.

FIG. 2C is a schematic view illustrating the structure by which the diaphragm adjusts the irradiation range.

FIG. 4A is the schematic diagram illustrating a subject area imaged to take a strip image relative to the target area.

FIG. 4B is the schematic view illustrating a mensurative X-ray image reconstructed by connecting the strip images.

FIG. 6A is the schematic diagram illustrating an ideal X-ray image incorporated in the pre-image.

FIG. 6B is the schematic diagram illustrating an X-ray image incorporated in the pre-image that is actually generated at the Step S1.

FIG. 7A is the schematic diagram illustrating an extraction process of the vertebra sideline.

FIG. 7B is the schematic diagram illustrating the extracted vertebra sideline.

FIG. 7C is the schematic diagram illustrating the extracted border line and the vertebral area.

FIG. D is the schematic diagram illustrating the third lumber vertebra and the center of the vertebra thereof.

Figure 8:
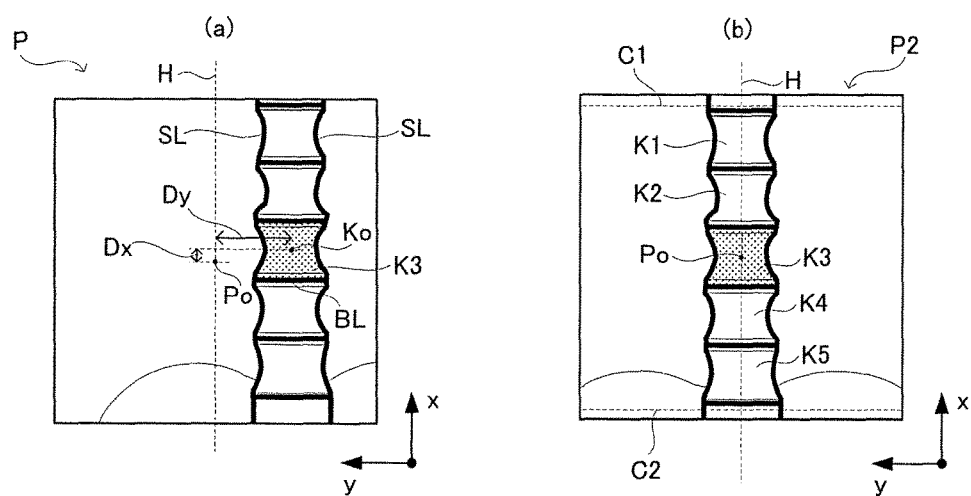

FIG. 8A, 8B are schematic diagrams illustrating processes of the Step S3 and the Step S4 according to the aspect of the Embodiment 1.

FIG. 8A is the schematic diagram illustrating a correction level based on the location of the center of the vertebra.

FIG. 8B is the schematic diagram illustrating a pre-image corrected based on the correction level as the Step 4.

Figure 9:
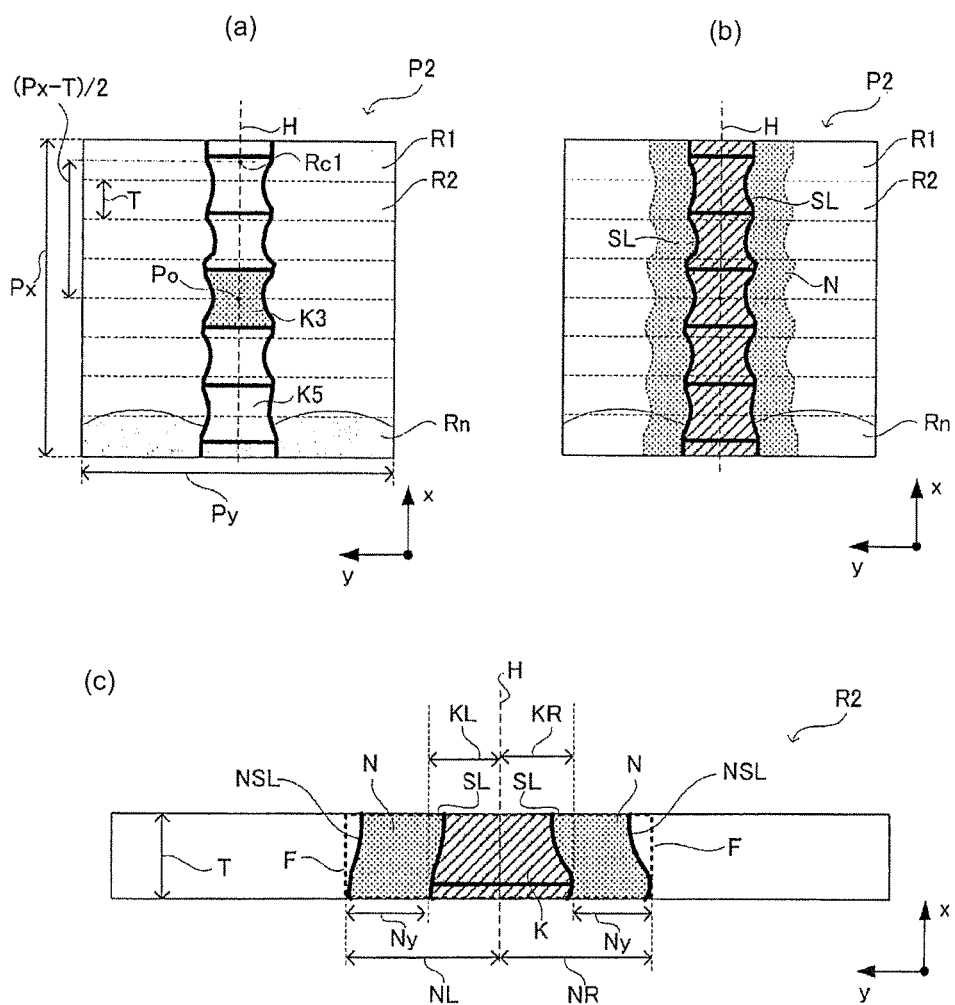

FIG. 9A, 9B, 9C are schematic diagrams illustrating a process of the Step S5 according to the aspect of the Embodiment 1.

FIG. 9A is the schematic diagram illustrating an imaging range of the strip image relative to the pre-image.

FIG. 9B is the schematic diagram illustrating the area subject to the bone densitometry relative to the pre-image.

FIG. 9C is the schematic diagram illustrating the calculation method of the aperture relative to each area.

FIG. 10A, 10B, 10C, 10D are schematic diagrams illustrating a process of the Step S6 according to the aspect of the Embodiment 1.

FIG. 10A is the schematic diagram illustrating the aperture of the diaphragm in the x-direction followed by shifting.

Figure 10:
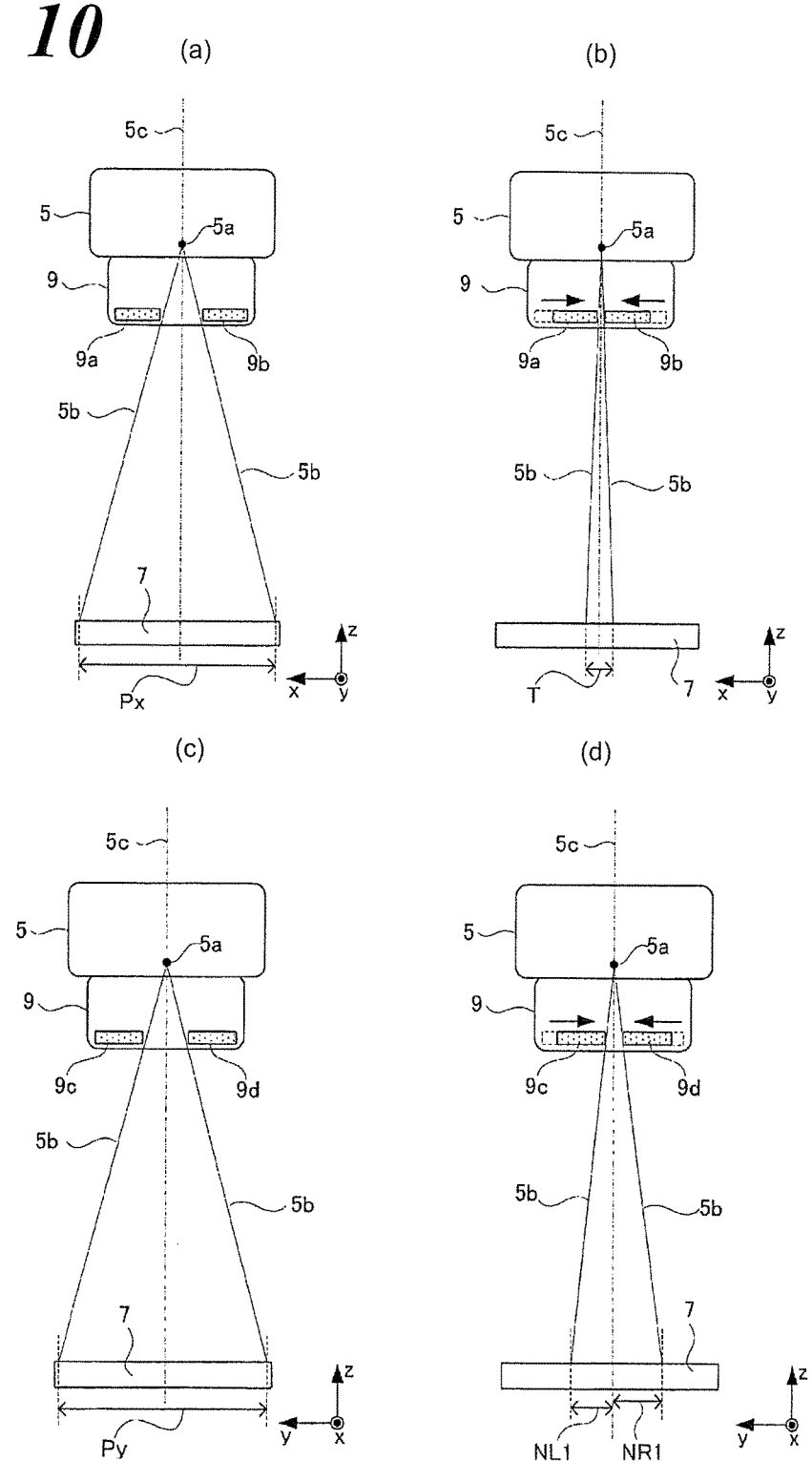

FIG. 10 is the schematic diagram illustrating the aperture of the diaphragm in the x-direction following shifting.

FIG. 10C is the schematic diagram illustrating the aperture of the diaphragm in the y-direction followed by shifting.

FIG. 10D is the schematic diagram illustrating the aperture of the diaphragm in the v-direction following shifting.

Figure 11:
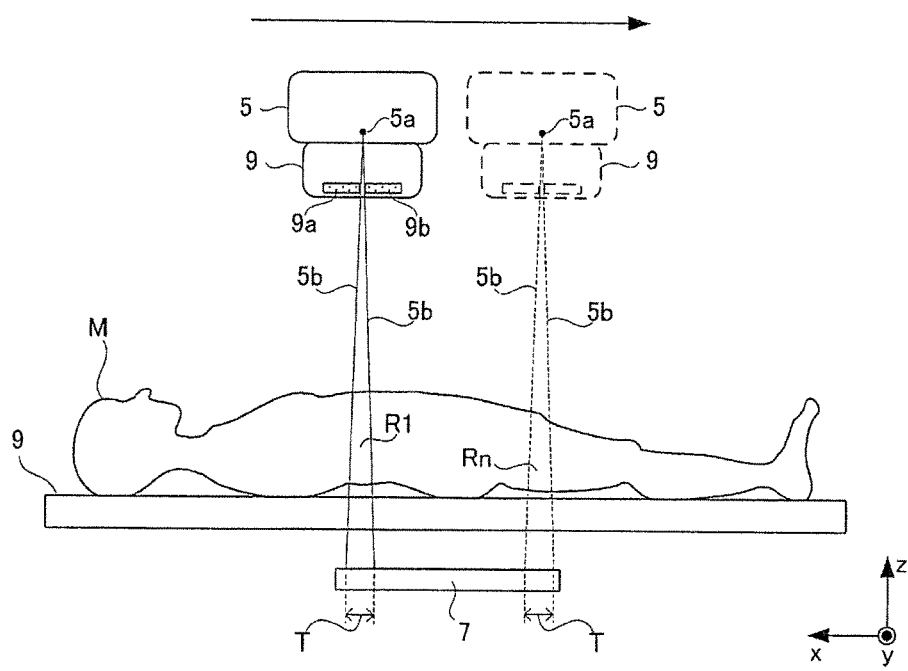

FIG. 11 is a schematic diagram illustrating an operation of the X-ray imaging apparatus at the Step S7 according to the aspect of the Embodiment 1.

Figure 12:
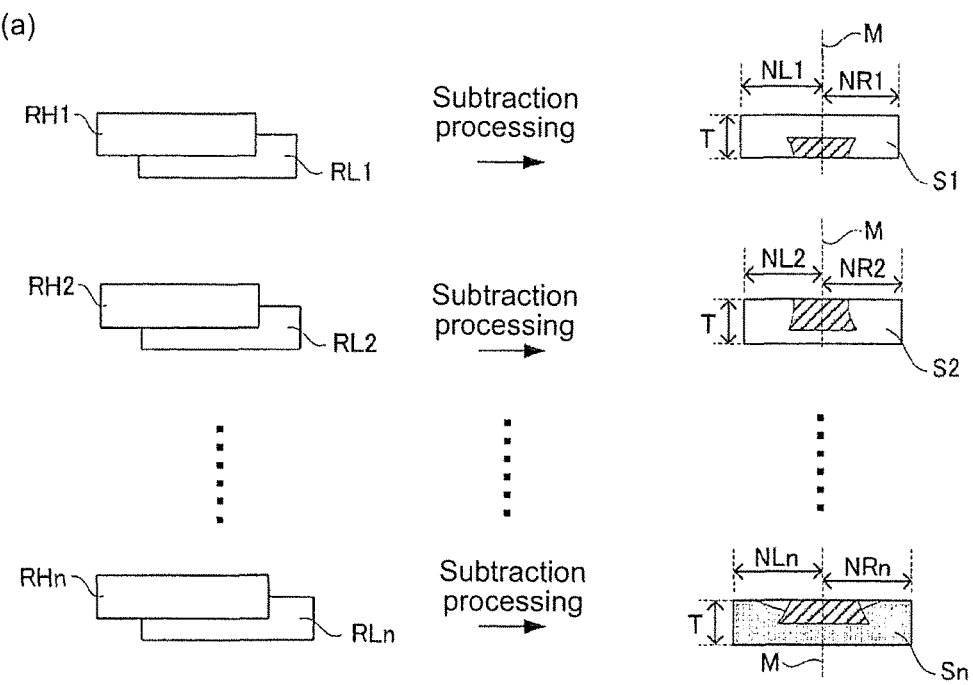
Figure 12:
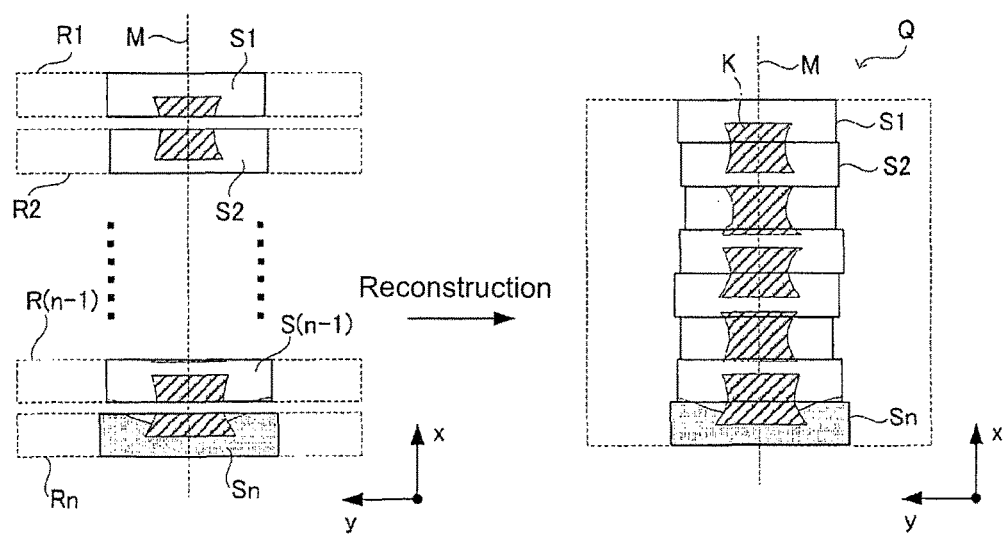

FIG. 12A, 12B are schematic diagrams illustrating processes of the Step S8 and the Step S9 according to the aspect of the Embodiment 1.

FIG. 12A is the schematic diagram illustrating a subtraction processing at the Step 8.

FIG. 12B is the schematic diagram illustrating a reconstruction processing at the Step 9.

Figure 13:
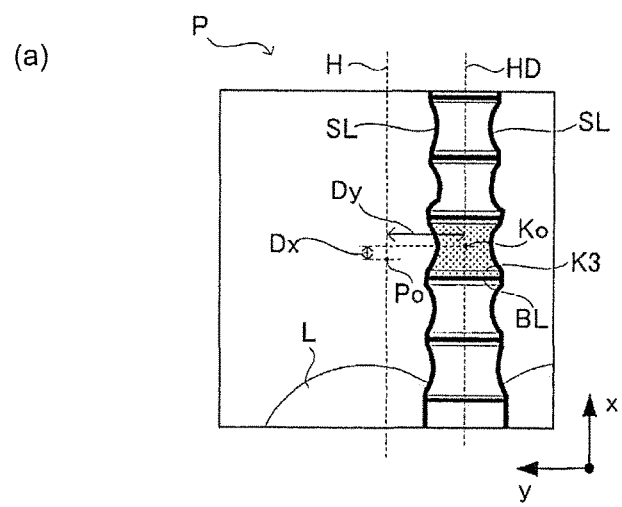
Figure 13:
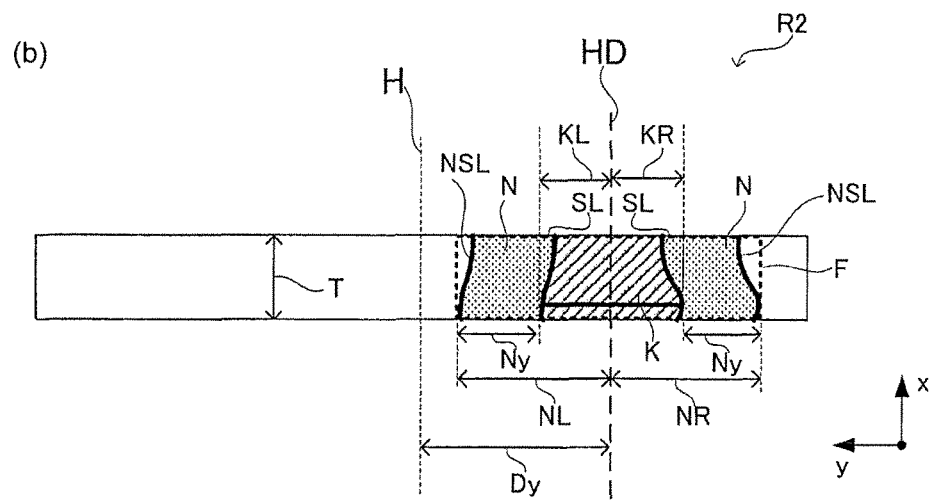

FIG. 13A, 13B are schematic diagrams illustrating an operation of the X-ray imaging apparatus of Embodiment 2.

FIG. 13A is a schematic diagram illustrating a correction level based on the location of the center of the vertebra and a straight line passing the center of the vertebra.

Figure 14:
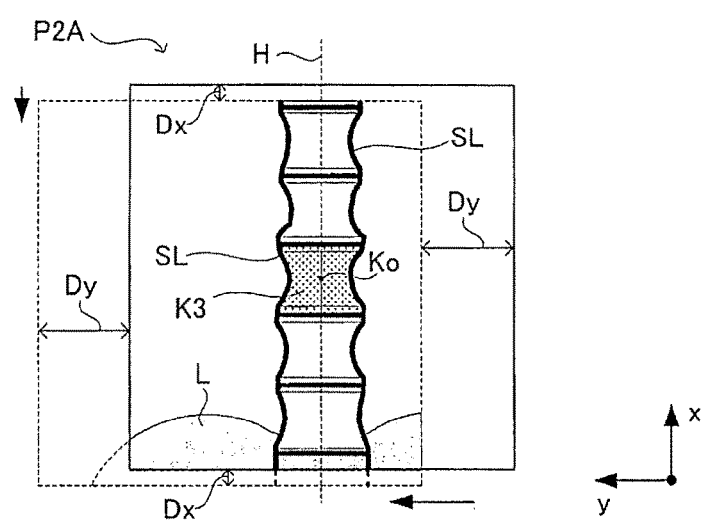

FIG. 14 is a schematic diagram illustrating a pre-image of which an imaging location is corrected virtually according to the aspect of the alternative Embodiment 2.

Figure 15:
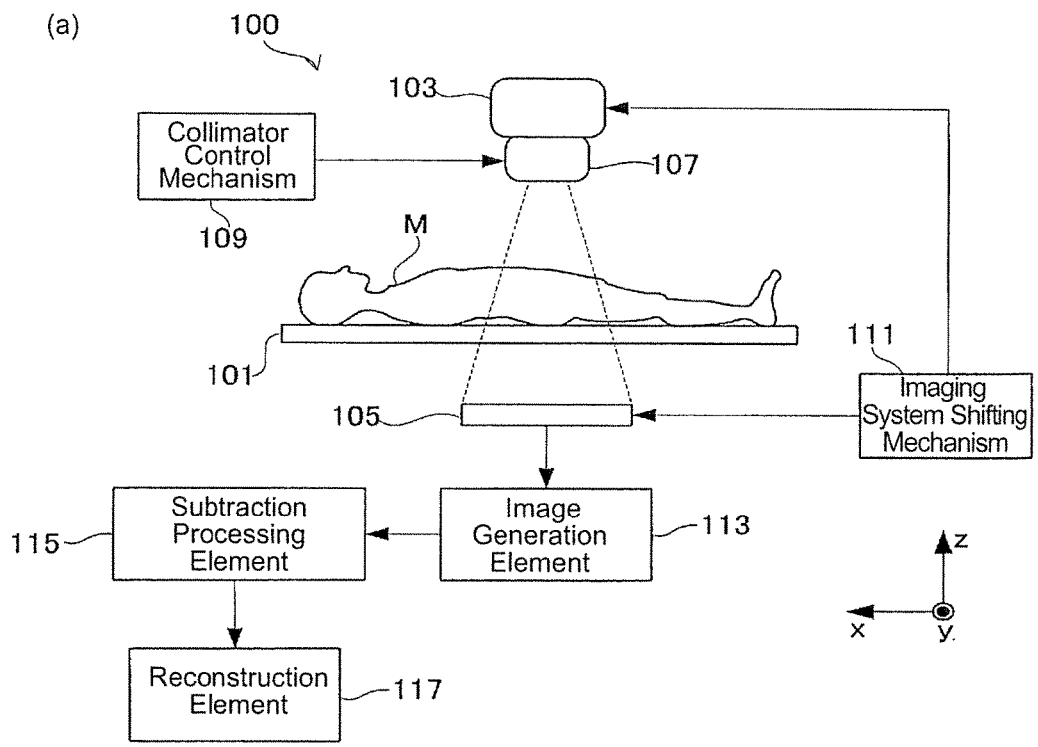
Figure 15:
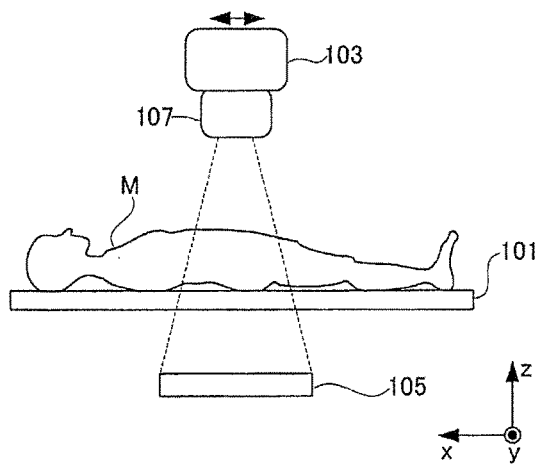
Figure 15:
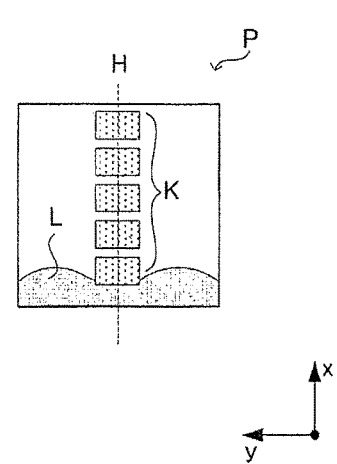

FIG. 15A, 15B, 15C are schematic diagrams illustrating an X-ray imaging apparatus according to the aspect of the conventional Example.

FIG. 15A is a schematic diagram illustrating the system of the X-ray imaging apparatus 1 according to the aspect of the conventional Example.

FIG. 15B is a schematic diagram illustrating an operation of the X-ray imaging apparatus 1 according to the aspect of the conventional Example.

FIG. 15B is a schematic diagram illustrating a pre-image according to the aspect of the conventional Example.

Figure 16:
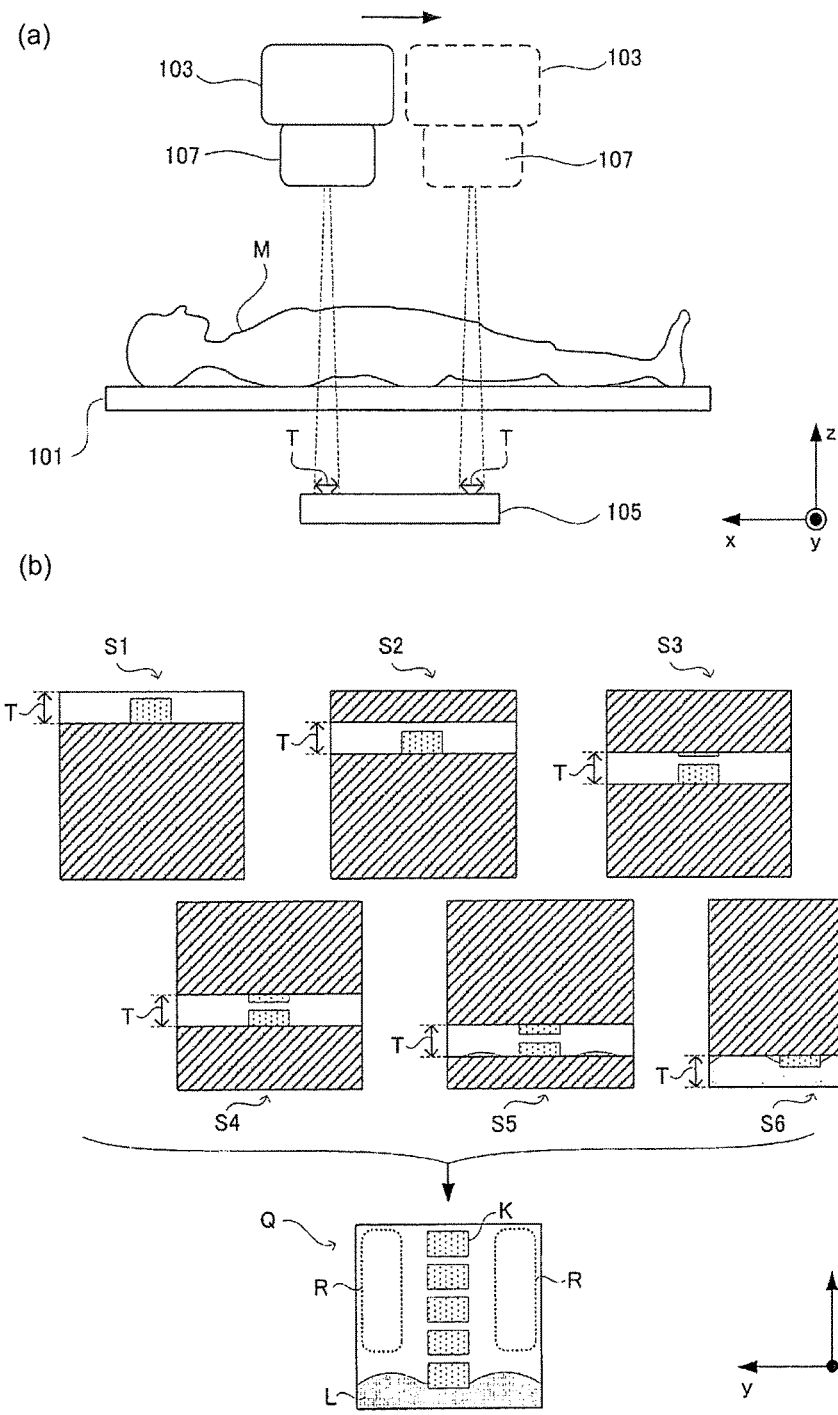

FIG. 16A, 16B are schematic diagrams illustrating an operation of the X-ray imaging apparatus according to the aspect of the conventional Example.

FIG. 16A is the schematic diagram illustrating a subtraction image according to the aspect of the conventional Example.

FIG. 16B is the schematic diagram illustrating a mensurative X-ray image reconstructed according to the aspect of the conventional Example.

DETAILED DESCRIPTION OF THE PREFERRED EMBODIMENTS

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Embodiment 1

Referring to FIGs, the inventors sets forth the Embodiment 1 of the present invention.

Illustration of the Entire Structure

Figure 1:
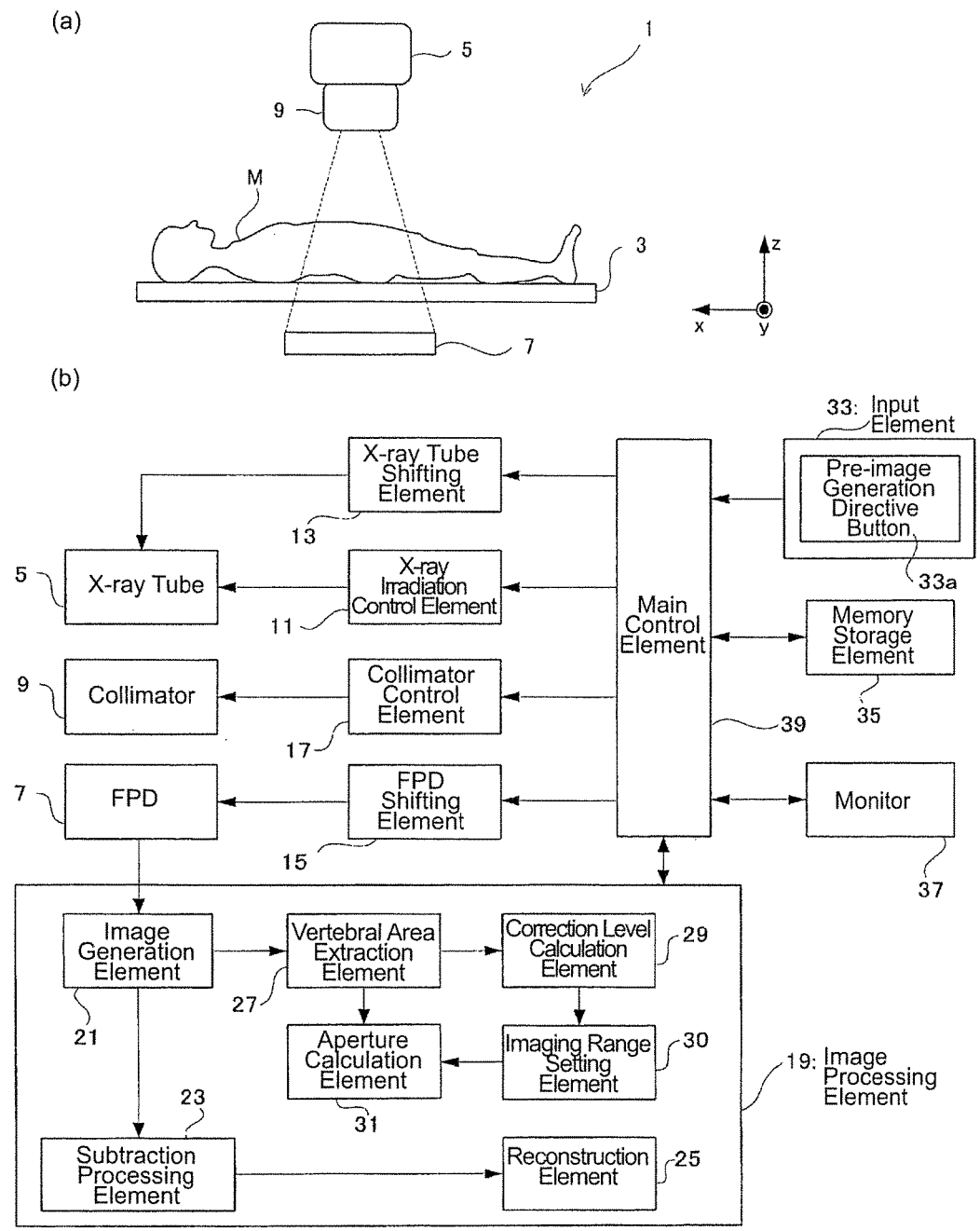
FIG. 1A is a schematic diagram illustrating the system of the X-ray imaging apparatus 1 according to the aspect of the Embodiment 1.
FIG. 1B is a block diagram illustrating the system of the X-ray imaging apparatus 1 according to the aspect of the Embodiment 1.

Referring to FIG. 1A, an X-ray imaging apparatus 1 according to the aspect of the Embodiment 1, comprises a tabletop 3 on which a subject M is in decubitus (lying down), an X-ray tube 5 that irradiates an X-ray to the subject M, and an FPD 7 that detects the X-ray irradiated to and transmitted through the subject M. The X-ray tube 5 and the FPD 7 are in-place facing each other sandwiching the tabletop 3. The FPD 7 comprises a detection surface that detects X-rays, on which surface the X-ray detection elements are 2-dimensionally arranged. The X-ray tube 5 corresponds to the radiation source of the present invention and the FPD 7 corresponds to the radiation detection means of the present invention.

Figure 2:
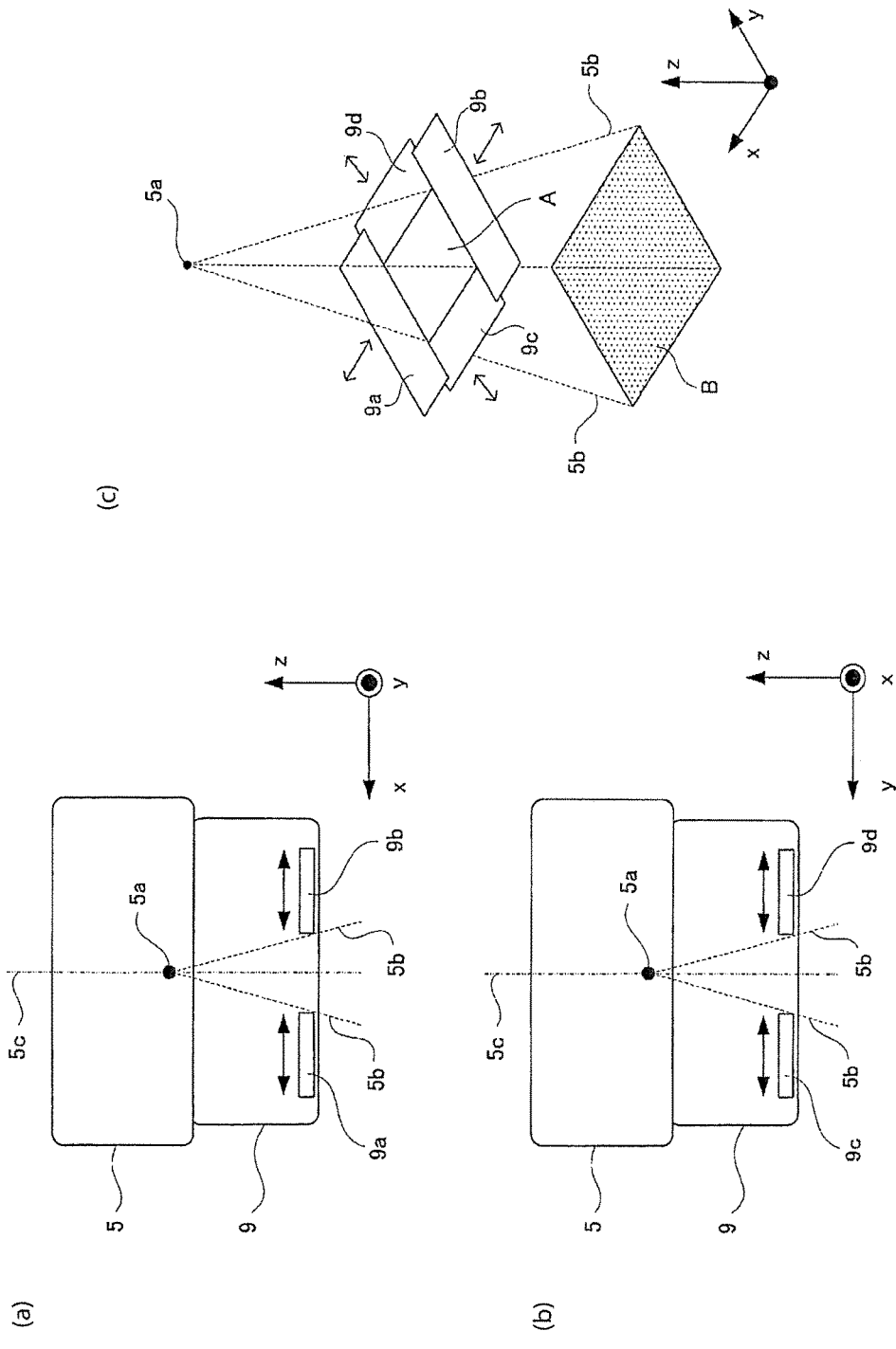
FIG. 2A, 2B, 2C are explanatory views illustrating a structure of a collimator according to the aspect of the Embodiment 1.

The collimator 9 that is installed under the X-ray tube 5 comprises 4 plate-like diaphragms $9a$–$9d$. Referring to FIG. 2A, the diaphragm $9a$ and the diaphragm $9b$ are shiftable in the x-direction (long side of the tabletop 3 and the body axis direction of the subject M), in which the center axis $5c$ of the X-ray $5b$ irradiated from the focal point $5a$ of the X-ray tube 5 is the base point. And referring to FIG. 2B, the diaphragm $9c$ and the diaphragm $9d$ are shiftable in the y-direction (short direction of the tabletop 3).

Each diaphragm $9a$–$9d$ is made of a material that can shield X-rays and the material therefor may include e.g., lead. Referring to FIG. 2C, broadening of the X-ray $5b$ irradiated from the focal point $5a$ of the X-ray tube 5 is limited by each diaphragm $9a$-$9d$ to provide a pyramid like shape. Then, the X-ray passing through the aperture A formed with respective diaphragms $9a$–$9d$ is irradiated to the subject M.

Specifically, the aperture A is adjusted by opening-and-closing the diaphragms $9ai$-$9d$ so that the location and the range of the irradiation field of X-ray $5b$ can be adjusted. In addition, the collimator 9 comprises a visible light lamp (not shown in FIG.) and it is adjusted so that the irradiation field of the visible light irradiated from the visible light lamp coincides with the irradiation field of the X-ray $5b$ irradiated from the focal point $5a$. The diaphragms $9a$-$9d$ correspond to shielding elements of the present invention.

Referring to FIG. 1B, the X-ray imaging apparatus 1 comprises an X-ray irradiation control element 11; an X-ray shifting element 13; a FPD shifting element 17; and an image processing element 19. The X-ray irradiation control element 11 connected to the X-ray tube 5 controls a dose of X-rays irradiated from the X-ray tube 5 and a timing of the X-ray irradiation and so forth by controlling an irradiation time period and a tube voltage that is added to the X-ray tube 5. The X-ray irradiation control element 11 corresponds to the irradiation control means of the present invention.

The X-ray tube shifting element 13 connected to the X-ray tube 5 shifts the X-ray tube 5 in the x-direction and the y-direction. The FPD shifting element 15 connected to the FPD 7 shifts the FPD 7 in the x-direction and the y-direction. Specifically, the imaging system comprising the X-ray tube 5 and the FPD 7 shifts horizontally in the x-direction and y-direction according to the X-ray shifting element 13 and the FPD shifting element 15.

The collimator control element 17 adjusts the irradiation field of the X-ray 5b irradiated from the X-ray tube 5 by controlling opening, closing and shifting of each diaphragm 9a-9d installed to the collimator 9. The X-ray tube shifting element 13 and the FPD shifting element 13 correspond to the imaging system shifting means of the present invention. The collimator control element 17 corresponds to the collimator control means of the present invention.

The image processing, element 19 comprises; an image generation element 21, a subtraction processing element 23; a reconstruction element 25, a vertebral area extraction element 27, an imaging range setting element 30 and an aperture calculation element 31. The image generation element 21 installed in the posterior of the FPD 7 generates the X-ray image of the subject M based on the X-ray detection signal output from the FPD 7.

The X-ray image generated by the image generation element 21 includes an X-ray image (pre-image) applied to set the imaging range of the mensurative X-ray image in addition to each strip-like X-ray image that is applied to reconstruct the mensurative X-ray image. In addition, a variety of X-ray images includes an X-ray image (high-voltage X-ray image) generated by the image generation element 21 when a high-voltage is added to the X-ray tube 5 and an X-ray image (low-voltage X-ray image) generated by the image generation element 21 when a low-voltage is added to the X-ray tube 5. The image generation element 21 corresponds to the strip image generation means and the pre-image generation means of the present invention.

A subtraction processing element 23 installed in the posterior of the image generation element 21 executes a subtraction processing in which the low-voltage X-ray image is subtracted from the high-voltage X-ray image. Hereinafter, an X-ray image generated by the subtraction processing is called the subtraction image. The subtraction processing element 23 corresponds to the subtraction processing means of the present invention.

The reconstruction element 25 installed in the posterior of the subtraction processing element 23 connects a series of generated subtraction images along the body axis direction of the subject M to reconstruct the mensurative X-ray image. The reconstruction element 25 corresponds to the reconstruction means of the present invention. In addition, the mensurative X-ray image corresponds to the combined image of the present invention.

The vertebral area extraction element 27 analyzes the X-ray image incorporated in the pre-image and extracts the area incorporating the vertebra image as a vertebral area. In addition, the vertebral area extraction element 27 extracts the center point of the vertebral area. The correction level calculation element 29 calculates the correction level of the imaging system based on the location of the center point of the vertebral area extracted by the vertebral area extraction element 27. The imaging range setting element 30 sets the location and the size of the imaging range (target area) of the mensurative X-ray image based on the correction level. In addition, the image range setting element 30 sets each location and size of the area at which the strip image is taken.

The aperture calculation element 31 calculates the aperture when each strip X-ray image is taken based on the vertebral area extracted by the vertebral area extraction element 27. Here, the aperture is an opening level of each diaphragm 9a☐9d that controls the range of the X-ray irradiation field. In addition, the inventor sets forth later relative to a method to calculate the correction level and the aperture. In addition, the imaging range calculation element 27 corresponds to the imaging range calculation means of the present invention. The correction level calculation element 29 corresponds to the correction range calculation means of the present invention. The aperture calculation element 31 corresponds to the aperture calculation means of the present invention.

The X-ray imaging apparatus 1 further comprises an input element 33, a memory storing element 35 and a main control element 39. The input element 33 to which an operator inputs a directive is e.g., a panel for a keyboard input and a panel for a touchpanel input. In addition, the input element 33 comprises the pre-image generation directive button 33a.

When the operator pushes down the pre-image generation directive button 33a, the X-ray tube 5 irradiates an X-ray for a predetermined short period of time under a fluoroscopic mode and the image generation element 21 generates a pre-image. The pre-image generation directive button 33a is not limited to a button structure and a kind of switch can be applied. The input element 33 corresponds to the correction means of the present invention. The pre-image generation directive button 33a corresponds the pre-image generation means of the present invention.

The memory storing element 35 stores a variety of parameters being referred for controlling the X-ray imaging apparatus 1, and a variety of X-ray images generated by the image generation element 21 and so forth. An example of the parameter referred for controlling the X-ray imaging apparatus 1 is a tube voltage and a tube electric current which are added to the X-ray tube 5. The monitor 37 displays a variety of X-ray images and pre-images. The main control element 39 comprehensively controls the X-ray irradiation control element 11, the X-ray tube shifting element 13, the FPD shifting element 15, the collimator control element 17, the image processing element 19 and the monitor 37, respectively. The monitor 37 corresponds to the display means of the present invention and the main control element 39 corresponds to the imaging system shifting control means according to the aspect of the Embodiment 1.

Detail Description of the Operation

Figure 3:
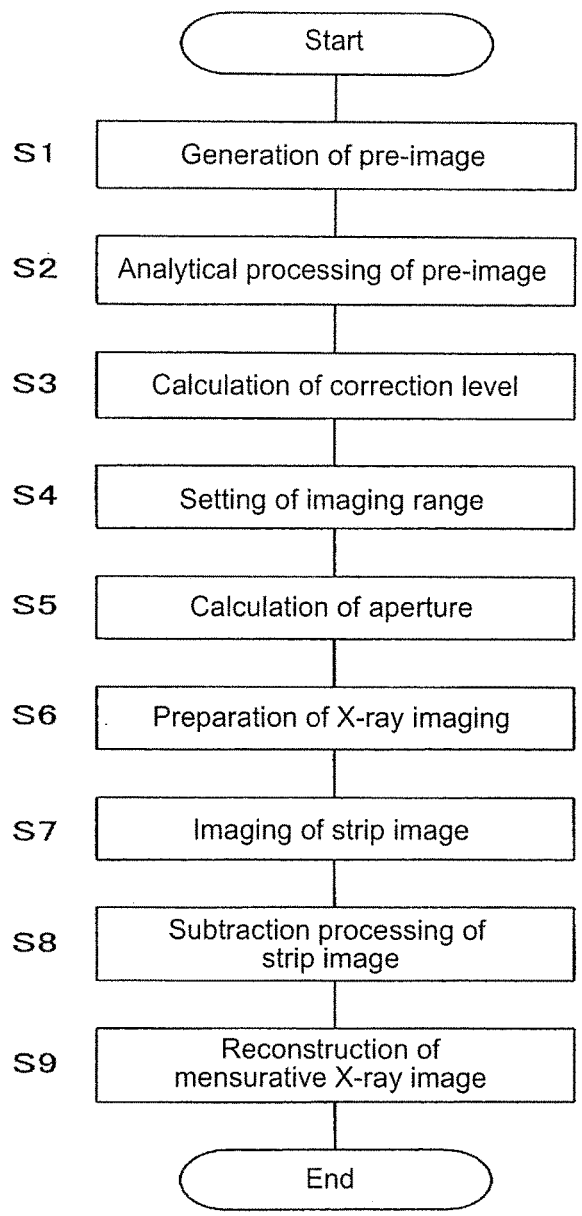
FIG. 3 is a flow chart illustrating an operation of the X-ray imaging apparatus of according to the aspect of the Embodiment 1.

Next, the inventor sets forth an operation to take an X-ray image applied to the bone densitometry, referring to the X-ray imaging apparatus 1 according to the aspect of the Embodiment 1. FIG. 3 is a flow chart illustrating an operation of the X-ray imaging apparatus of according to the aspect of the Embodiment 1.

The operation explanation illustrates the aspect of a reconstruction method of a single mensurative X-ray image by connecting the strip images along the body axis direction of the subject M following obtaining of multiple narrow and long rectangular X-ray images, of which the short direction is the body axis direction of the subject M, i.e., strip images.

Figure 4:
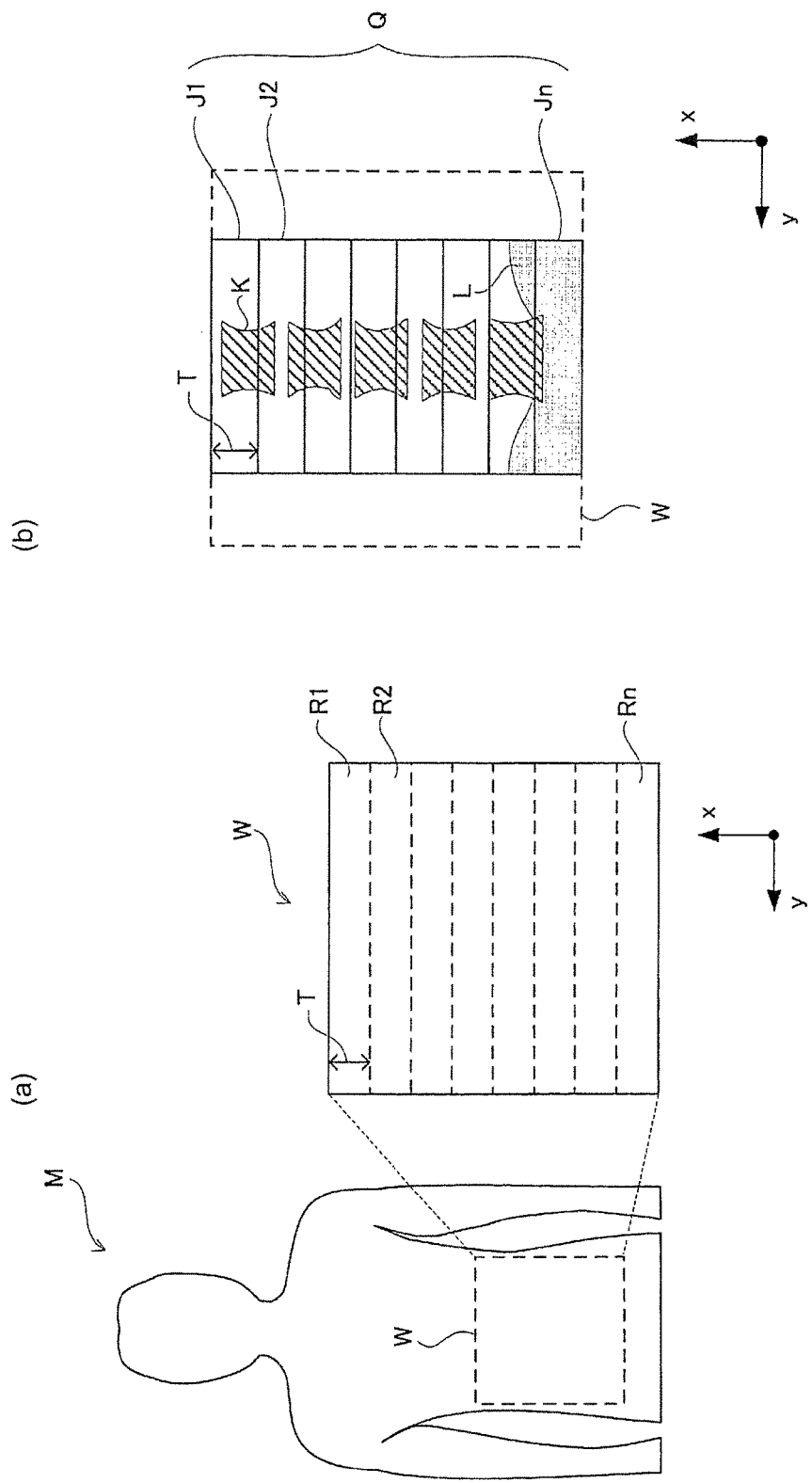
FIG. 4A, 4B are schematic views illustrating an operation of the X-ray radiographic apparatus of Embodiment 1.

Specifically, referring to FIG. 4A, the target area W of the subject M comprises multiple strip-shaped areas R1-Rn. And the strip image J1-Jn showing the vertebra K and the pelvis L are taken relative to the respective areas R1-Rn by the imaging operation of the X-ray imaging apparatus 1.

And referring to FIG. 4B, the mensurative X-ray image Q, which is applied to the bone densitometry of the target area W, is reconstructed by connecting the strip images J1-Jn along the body axis direction of the subject M. In addition, the length of the short direction of the respective strip images J1-Jn is T. Hereafter, the inventor sets forth each detail step of the operation steps.

Step S1 (Generation of a Pre-Image)

Firstly, the pre-image is generated to take a mensurative X-ray image X-ray image which is applied to the bone densitometry. The pre-image is an X-ray image that is applied to set the imaging range of the mensurative X-ray image. First, the operator loads the subject M on the tabletop 3 so that the body axis direction of the subject M coincides with the x-direction.

Figure 5:
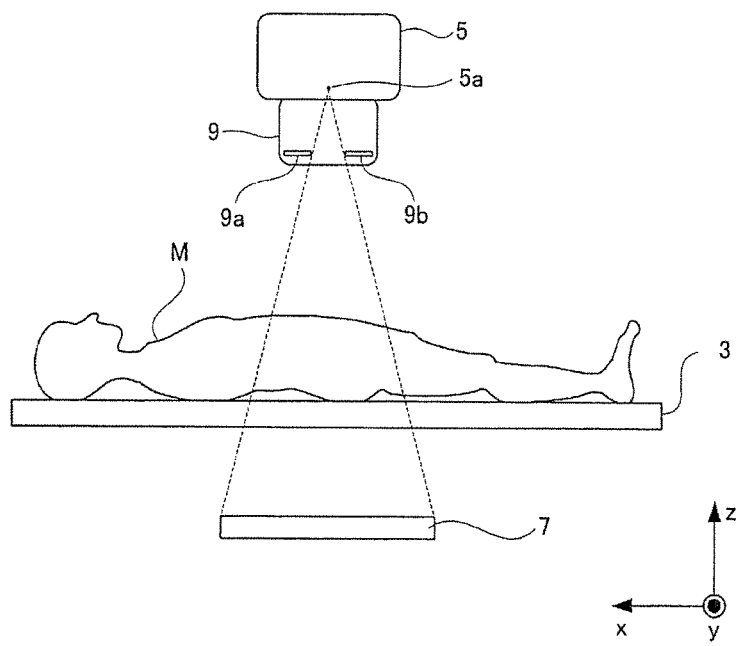
FIG. 5 is a schematic diagram illustrating an operation of the X-ray imaging apparatus at the Step S1.

Then, the operator makes sure the irradiation field of the visible light irradiated from the collimator 9 and so forth, determines the approximate imaging location (location of the imaging system) of the pre-image, and respectively shifts the X-ray tube 5 and the FPD 7 to the location indicated in FIG. 5. In addition the bone densitometry is performed mainly based on the X-ray image of the lumber vertebra, so that the imaging location of the pre-image corresponds to the proximity of the low back (lumber area).

The operator directs generation of the pre-image by operating the input element 33 following shifts of the image system (X-ray tube 5 and FPD 7). The directive of the pre-image generation is carried out by pushing down the pre-image generation directive button 33a installed in the input element 33. At this time, values of the tube voltage and the tube electric current, which provides a lower X-ray dose than the dose for X-ray imaging, to perform an X-ray fluoroscopy.

The data input in the input element 33, such as the tube voltage and the tube electric current, are sent to the main control element 39. In addition, when the pre-image generation directive button 33a is pushed down, the data indicating that the irradiation time is a predetermined short time is sent from the input element 33 to the main control element 39. The main control element 39 outputs the control signal to the X-ray irradiation control element 11 based on the receiving data.

The X-ray irradiation control element 11 irradiates a cone-beam-like X-ray 5b from the focal point 5a of the X-ray tube 5 to the subject M for the predetermined short period of time according to the control signal. According to the aspect of the Embodiment 1, the predetermined short period of time in-between the X-ray 5 irradiation is the time corresponding to one pulse of the X-ray beam. And an example of the time corresponding to one pulse of the X-ray beam is in the approximate range of 3 ms (millisecond) to 10 ms. In addition, the X-ray 5b irradiation time corresponding to the predetermined short period is not limited to one pulse of the X-ray beam and can be changed to a few pules of X-ray beams as needed.

In such case, the time while the X-ray is irradiated to generate the pre-image is extremely short, so that the radiation doe to the subject M can be restrained. In addition, the X-ray is irradiated for the predetermined short period by pushing down the pre-image generation directive button 33a. Specifically, the X-ray irradiation time is always a predetermined short period regardless how long the pre-image generation directive button 33a has been pushed down. Therefore, the x-ray irradiation time can be absolutely short as is predetermined by such simple operation. As results, it is absolutely avoidable that the X-ray irradiation time is different from one generated pre-image to the other.

The irradiated X-ray 5b transmits the subject M and is being detected by the FPD 7. The FPD 7 outputs an X-ray signal based on the detected X-ray. The image generation element 21 generates a pre-image showing the vertebra K and the pelvis L of the lumber vertebra based on the detected X-ray signal. The generated pre-image P is sent to the vertebral area extraction element 27 and stored in the memory storing element 35. The main control element 39 displays the stored pre-image P as a still image on the monitor 37.

Step S2 (Analytical Processing of a Pre-Image)

Figure 6:
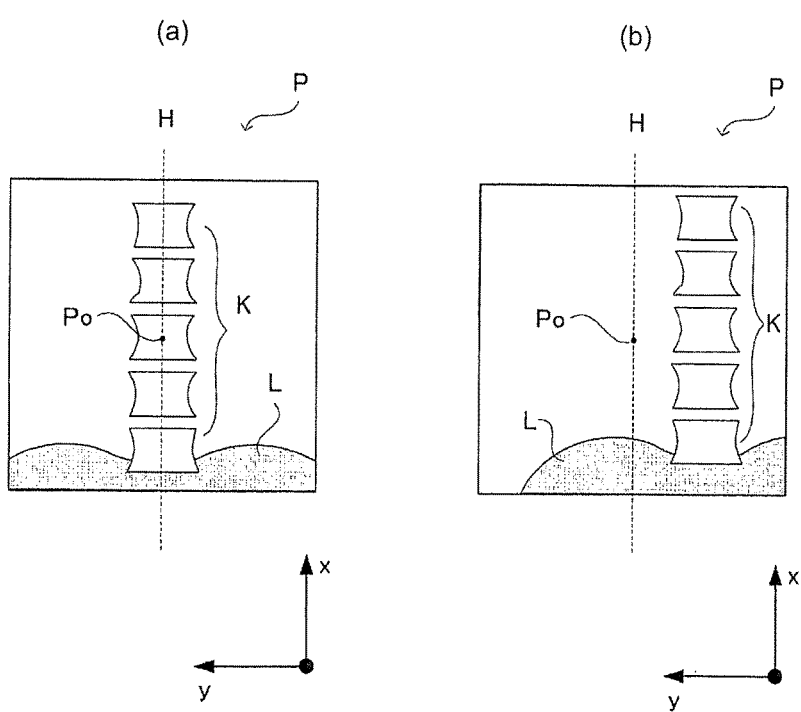
FIG. 6A, 6B are schematic diagrams illustrating a process of the Step S1 according to the aspect of the Embodiment 1.

Relative to the generated pre-image, per se, it is ideal that the vertebra K of the lumber vertebra is respectively shown on the center line of the y-direction and the center of the entire 5 vertebrae K coincides with the center Po of the pre-image P (referring to FIG. 6A). However, in fact, each vertebra K appears in the location out of the center line of the pre-image due to the shift of the location for imaging (location of the imaging system) and so forth (referring to FIG. 6B). In such case, the imaging location for the pre-image P must be corrected to be the appropriate location to obtain the mensurative X-ray image more suitable for the bone densitometry.

Then, the operator performs on the analytical processing of the pre-image P to correct the imaging location so as to be an appropriated location. Referring to FIG. 6B, the vertebral area extraction element 27 extract the vertebral area of the respective vertebrae K from the pre-image P when the analytical processing of the pre-image is executed. The steps of extracting the vertebral area are distinguished to mainly two steps. One step is an extraction step to extract the sideline profile of the vertebra K and another step is an extraction step to extract an individual vertebra by extracting the borderline of the vertebrae adjacent each other.

First of all, the vertebral area extraction element 27 executes a processing to extract the side-profile (sideline) profiling the vertebra K relative to the pre-image P. The sideline extraction is executed by searching pixels forming the sideline relative to the pixel line in the v-direction of each coordination x of the pre-image P.

Figure 7:
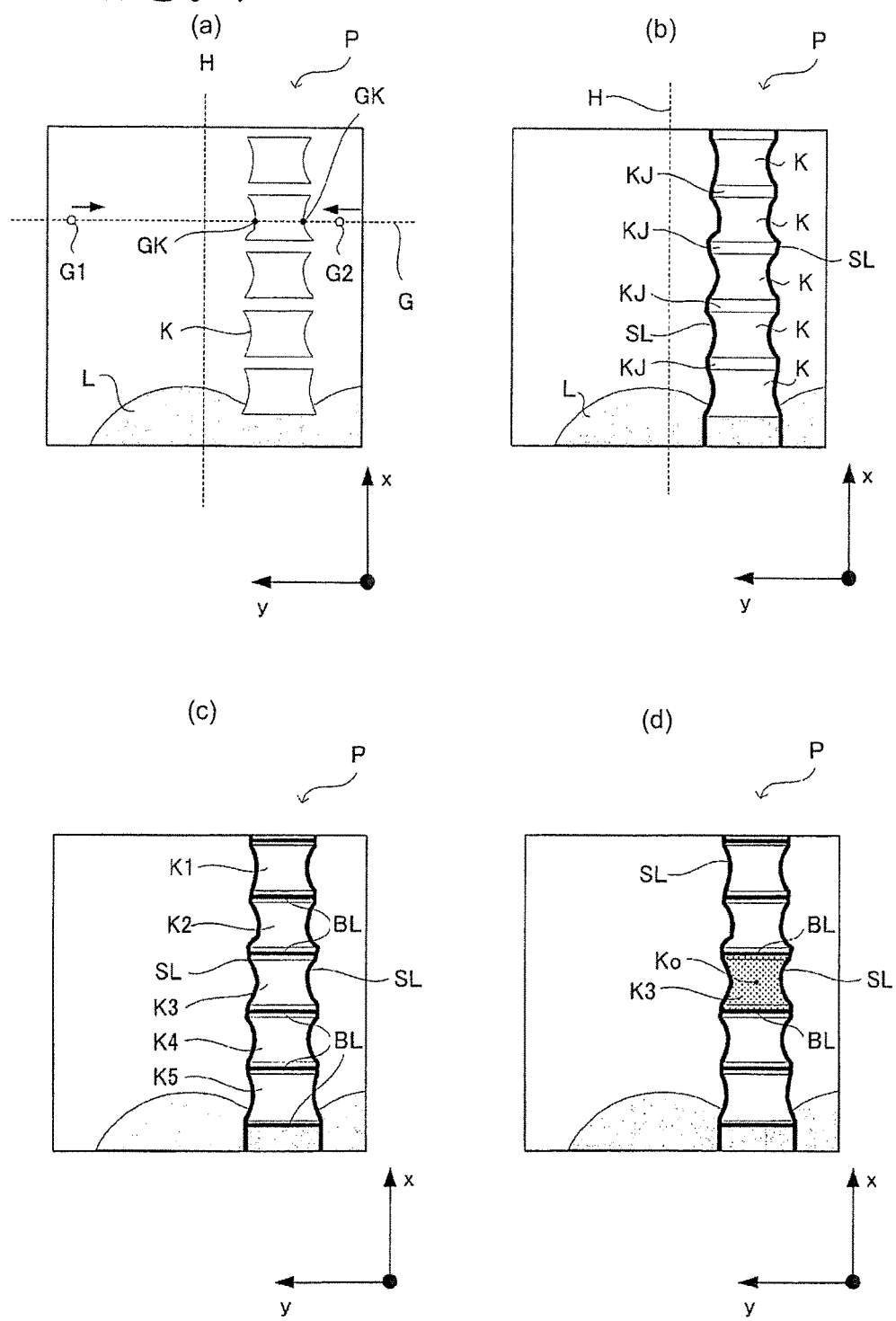
FIG. 7A, 7B, 7C, 7D are schematic diagrams illustrating a process of the Step S2 according to the aspect of the Embodiment 1.

Here, referring to FIG. 7A, the inventor sets forth the search method of the pixel forming the sideline using the sideline G extending in the y-direction as an example. First, the right and left locations in a constant distance from the center line H are determined as the initial search location G1 and G2 on the pixel line G. Then, the search begins form G1 and G2 to the center line H. Then, the location of the pixel GK forming the sideline of the pixel line G is extracted by referring the gradient of each pixel of the pixel line G and the location of the pixel of other x-coordination already extracted as a sideline.

In such way, the respective locations forming the sideline are extracted relative to the pixel line in the y-direction of each x-coordination and the locations of the respective extracted pixels are connected to each other. As results, two of the sidelines SL of the vertebra K extending in the x-direction are extracted (referring to FIG. 7B). Not only the actual side profile of the vertebra K can be confirmed by referring the sideline SL, but also the profile corresponding to the vertebral area even in the upper and lower areas outside the vertebra K, e.g., such as the inside of the pelvis L.

And the vertebral area extraction element 27 extracts the borderline of the vertebra. An intervertebral disc space KJ between the vertebrae adjacent each other exists. Referring to FIG. 7C, the borderline BL between the vertebrae K is extracted by drawing in the center of intervertebral disc space KJ. As results, five vertebral areas are extracted as areas surrounded by the sidelines SL and the borderlines BL in the pre-image. In addition, the vertebral area including the first lumber vertebra is the vertebral area K1, and the vertebral areas including the respective lumbar vertebrae between the second lumber vertebra and the fifth lumber vertebra are respectively the vertebral area K2-K5. In addition, the vertebral areas K1-K5 corresponds to the feature areas of the present invention.

The vertebral area extraction element 27 detects the vertebral area K3, which is indicated by the shaded area in FIG. 7D and includes the third lumber vertebra K3, among the extracted vertebral areas K1-K5. Further, the vertebral area extraction element 27 extracts the point, which is the center of the vertebral area K3, as the vertebral center Ko. The vertebral center Ko is an approximate center point of the entire vertebral areas comprising the vertebral areas K1-K5.

The respective vertebral areas K1-K5 and the vertebral center Ko are extracted, so that the analytical processing of the pre-image P can be completed and the image data of the pre-image P on which the analytical processing was performed can be sent to the correction level calculation element 29. Further, the pre-image P following the analytical processing is stored in the memory storing element 35 and displayed on the monitor 37. The operator can confirm the location of the extracted vertebral center by referring the pre-image P appearing on the monitor 37.

Step S3 (Calculation of the Correction Level)

The correction level calculation element 29 calculates the correction level based on the analysis-processed pre-image P following completion of the analytical processing of the pre-image. The correction level is a shift distance of the imaging location (location of the imaging system) to correct the pre-image.

As the bone densitometry is carried out based on the X-ray image of the lumber vertebra, it is preferable that the correction of the imaging location is executed so that the vertebral center Ko appeared in the pre-image P can coincide with the center of the pre-image P. Specifically, referring to FIG. 8A, the correction level is calculated as the distance Dx in the x-direction and the distance Dy in the y-direction from the vertebral center Ko to the center of the pre-image P.

Step S4 (Setting of the Imaging Range)

The setting of imaging range of the mensurative X-ray image Q is executed based on the correction level following calculation of the correction level. According to the aspect of the Embodiment 1, the correction of the imaging range of the pre-image is executed prior to setting of the imaging range of the mensurative X-ray image Q. The operator shifts the location of the imaging system by operation the input element 33 so that the center of the pre-image can coincide with the center of the feature area. Specifically, the X-ray tube shifting element 13 and the FPD shifting element 15 shift each element of the imaging system in the x-direction by the distance Dx and in the y-direction by the distance Dy based on the correction level.

And the operator pushes down the pre-image generation directive button 33a, so that an X-ray under a fluoroscopic mode can be irradiated for a predetermined short period to regenerate the pre-image. The pre-image that is regenerated following correction of the imaging location is a pre-image P2. The pre-image P2 is displayed on the monitor 37.

And the vertebral area extraction element 27 performs the analytical processing on the pre-image P2 following the correction to extract the sideline SL, the vertebral areas K□K5 and the vertebral center Ko. Referring to FIG. 8B, relative to the pre-image P2, the vertebral center Ko is corrected to coincide with the center Po thereof. Specifically, the correction level at the imaging location of the pre-image P2 is zero (null). The operator confirms whether the location of each vertebral area and the location of the vertebral center Ko are appropriately corrected or not by referring the pre-image P2 displayed on the monitor 37.

In addition, if it is determined that an automatic correction based on the correction level is unsatisfactory by referring the pre-image P2 and if needed, the operator further operates the input element 33 so that the imaging location of the pre-image P2 can be manually corrected as needed. In addition, the operator can as needed correct each location of the sideline extracted by the vertebral area extraction element 27, the borderline BL and the vertebral center Ko by operating the input element 33. The image data of the pre-image P2 on which the analytical processing is performed is sent to an imaging range setting element 30.

Following confirmation of the imaging location of the pre-image P2, the imaging range of the mensurative X-ray image Q is set. The imaging range setting element 30 sets the location of the center of the imaging range (target area) of the mensurative X-ray image based on the correction level. Specifically, the central location of target area W is set so that the center of the target area W can coincide with the center Po of the pre-image P2. In such case, the vertebral center Ko coincides with the center of the imaging range of the mensurative X-ray image Q, so that the mensurative X-ray image Q can be an X-ray image suitable for observation of each vertebra. Accordingly, the correction level can be calculated by generating one piece of the pre-image P2 and in addition, the central location of the target area W can be set based on the correction level.

The operator operates the input element 33 referring the pre-image P2 to input the data of the length T of the strip image in the x-direction and the data of the length Px of the target area W in the x-direction. In addition, one example of the length of Px is approximately 9 inches (approximately 23 cm) and one example of the length T is approximately 2 cm. The center of the target area W is set based on the correction level, so that the imaging range setting element 30 can set the imaging range of mensurative X-ray image Q based on the length Px of the target area W in the x-direction.

According to the aspect of the Embodiment 1, it deems that the image range of the mensurative X-ray image Q coincides with the imaging range of the pre-image P2. Specifically, the length Px of the mensurative X-ray image Q in the x-direction coincides with the length of the pre-image P2 in the x-direction. The imaging range setting element 30 sets the location of the strip-like areas R1-Rn, in which each strip image can be imaged, and the number of the areas (number of n) based on the imaging range of the mensurative X-ray image Q, the value of the length Px and value of the length T. A variety of data including the image of the pre-image P2, on which the analytical processing is performed, the location of the target area W, and the location and the number of areas R1-Rn are sent to the aperture calculation element 31.

Step S5 (Calculation of the Aperture)

The aperture is calculated following regeneration of the per-image by shifting the imaging location and setting of the imaging range of the mensurative X-ray image. Here, the aperture is an opening level of the diaphragms 9a-9d when the respective strip images are taken.

Relative to the conventional apparatus, any length of the areas R1-Rn in the x-direction coincides with the length of the pre-image P2 in the y-direction. However, when the bone densitometry is actually carried out, the area incorporating the vertebra of the lumber vertebra as the target and the proximity of the vertebra having the variation of brightness is below the constant level are applied to the analysis. Specifically, the area having the X-ray image actually applied to the bone densitometry is limited to the vertebral area indicated by the diagonal lines (area sandwiched by the sidelines SL) and the proximity area of the vertebra indicated by the shade referring to FIG. 9B.

Therefore, when the mensurative X-ray image Q is obtained according to the conventional example, the X-ray is irradiated to even e.g., a flank and so forth which is unrelated area to the bone densitometry, so that the radiation dose to the subject can increase. In addition, each vertebra of five lumbar vertebrae has a different length in the y-direction depending on the region. Accordingly, the area needed to be imaged with an X-ray has respectively different length in the y-direction relative to the respective areas R1-Rn.

Then, the X-ray imaging apparatus 1 according to the aspect of the Embodiment 1 detects the imaging range of the strip image relative to the respective areas R1-Rn and calculates the aperture based on the detection. Hereinafter, referring to FIG. 9C, the inventor sets forth the calculation mechanism for the aperture relative to e.g., area R2. In addition, the right- and left-sideline are indicated by the sign NSL relative to the proximity area of the vertebra.

FIG. 9C is a schematic enlarged view illustrating the pre-image P2 relative to the area R2. An area needed to provide the strip image area in the area R2 is the area including the vertebral area K and the proximity area N of the vertebra, i.e., the area F surrounded by the broken line in FIG. 9C. The left edge of the area F contacts to the left sideline NSL at the farthest location from the center line H. The right edge of the area F contacts to the right sideline NSL at the farthest location from the center line H. The distance from the center line H to the left edge is NL and the distance from the center line H to the right edge is NR. In such case, the area F having the length T in the x-direction and the length of the sum of NL and NR is calculated as a strip-shaped area.

When the bone densitometry is executed, empirically the area that shifts laterally and parallel within the predetermined distance Ny from the vertebral area K indicated by the orthogonal lines is the proximity area N of the vertebra. The predetermined distance Ny is an empirical value applied to the bone densitometry, so that the value of the distance Ny can be calculated as the constant α. Here, the maximum distance from the center line H to the left sideline SL is KL and the maximum distance from the center line H to the right sideline SR is KR. In addition, following smoothing of the sideline SL by performing a smoothing processing on the respective sidelines SL, the distance KL and the distance KR can be applied.

In such case, the distance NL that is the distance from the center line H to the left edge of the area F can be calculated using the following mathematical formula (1) including the distance KL and the constance α

$$NL = KL + Ny = KL + \alpha \quad (1)$$

Also, the distance NR that is the distance from the center line H to the right edge of the area F can be calculated using the following mathematical formula (2) including the distance KR and the constance α

$$NR = KR + Ny = KR + \alpha \quad (2)$$

Accordingly, the aperture calculation element 31 can detect the location and the range of the area F that is the imaging range of the strip image relative to the area R2 by detecting the respective maximum distances from the center line H to the right- and left-sideline SL. The area F corresponds to the X-ray irradiation field when imaging the strip image relative to the area R2. Therefore, the aperture calculation element 31 can calculate the opening-and-closing level relative to the area R2 based on the location and the range of the area F.

The aperture calculation element 31 calculates an aperture based on the maximum distance from the center line H to the right- and left-sideline SL relative to the respective areas R1-Rn. In addition, the aperture calculated relative to the area R1 is V1, and then each aperture calculated relative to the areas R2-Rn is respectively V2-Vn. In addition, the value of the distance NL calculated relative to the respective areas R1-Rn is NL1-NLn hereinafter. And, the value of the distance NR calculated relative to the respective areas R1-Rn is NR1-NRn hereinafter. In addition, the respective detected areas F relative to the areas R1-Rn are respectively the areas F1-Fn.

Accordingly, the apertures V1-Vn are calculated relative to the respective areas R1-Rn based on the width of the vertebral area of the pre-image P2, and the data of each calculated aperture are stored in the memory storing element 35. When the respective apertures V1-Vn are calculated, the step of the Step 5 is completed.

Step S6 (Preparation For the X-Ray Imaging)

A preparation for the X-ray imaging is carried out following completion of the aperture calculation. According to the aspect of the Embodiment 1, it is given that first the X-ray imaging is performed on the area R1 and then each X-ray imaging of the R2, . . . , Rn is performed in turn. At this time, the operator shifts the X-ray tube 5 to the imaging location of the strip image relative to the area R1 by operating the input element 33 and together, adjusts the X-ray irradiation field. The imaging location of the strip image relative to the area R1 corresponds to the center Rc of the area R1 (referring to FIG. 8A). Specifically, the X-ray tube 5 shifts the distance (Px-T)/2 in the x-direction from the location corresponding to the center Po of the pre-image P2 to the location corresponding to the center Rc1 of the area R1.

And the diaphragms 9a and 9b shift from the locations indicated in FIG. 10A to the location indicated in FIG. 10B in the x-direction under the control of the collimator control element 17. As results, the X-ray 5b irradiated from the focal point 5a is limited from the cone beam broadening in the x-direction and the y-direction (referring to FIG. 10A) to the fan beam (referring to FIG. 9B) having the thickness T in the x-direction.

Further, the diaphragms 9c and 9d shift from the locations indicated in FIG. 10C to the location indicated in FIG. 10D in the x-direction under the control of the collimator control element 17. As results, the broadening of the X-rays 5b irradiated from the focal point 5a in the y-direction, which is the length Py in the y-direction of the pre-image P (referring to FIG. 10C), is limited the length corresponding to the aperture V1 (referring to FIG. 10D). Specifically, if the baseline is the center axis 5c of the X-rays 5b, the left side broadening in the y-direction is limited to NL1 and the right side broadening in the y-direction is limited to NR1, respectively.

As the respective diaphragms 9a-9d shift, the irradiation field of X-rays coincide with the range of the area F1. Following shift of the X-ray tube 5 and adjustment of the irradiation field of the X-ray, the preparation for X-ray imaging is completed.

Step S7 (Imaging a Strip Image)

Imaging for the strip image is performed following completion of the X-ray imaging preparation. Specifically, the operator directs to irradiate the X-ray 5b from the focal point 5a of the X-ray tube 5 by operating the input element 33. At this time. X-ray irradiation conditions including the tube voltage and so forth are input to perform the X-ray imaging under the imaging mode in which the X-ray dose is higher than the dose for an X-ray fluoroscopy. The FPD 7 detects the X-ray 5b transmitted through the area F of the subject M and outputs an X-ray signal. The image generation element 21 generates strip images based on the received X-ray detection signals.

In addition, the imaging for the strip image under the imaging mode is performed twice at the same imaging location or almost the same imaging location. Specifically, the operator inputs the directive so as to add relatively high tube voltage to the X-ray tube 5 on the first imaging. In such case, the image generation element 21 generates the strip image based on the high-voltage thigh-voltage strip image). In addition, the high-voltage strip images that is generated relative to the respective areas R1-Rn are respectively the high-voltage strip images RH1-RHn.

And the operator inputs the directive to add relatively low tube voltage to the X-ray tube 5 on the second imaging. In such case, the image generation element 21 generates the strip image based on the low-voltage (low-voltage strip image). In addition, the low-voltage strip images that is generated relative to the respective areas R1-Rn are respectively the low-voltage strip images RL1-RLn. The X-ray imaging at the area R1 ends when the high-voltage strip image RH1 and the low-voltage strip image RL1 are imaged. The imaging order relative to the high-voltage strip image RH1 and the low-voltage strip image RL1 can be reversed.

The X-ray imaging relative to the area R2 is performed following completion of the X-ray imaging relative to the area R1. The X-ray tube shifting element 13 shifts the X-ray tube 5 to the imaging location of the strip image relative to the area R2. And the collimator control element 17 shifts the diaphragm 9c and the diaphragm 9d to the location corresponding to the aperture V2. Specifically, if the baseline is the center axis 5c of the X-rays 5b, the diaphragm 9c and the diaphragm 9d shift respectively in the y-direction so that the left side broadening of the X-ray 5b in the y-direction can be NL2 and the right side broadening thereof in the y-direction can be NR2. And the X-ray tube 5 performs the X-ray irradiations twice following completion of the shift of the X-ray tube 5 and control of the collimator 9. As results, the image generation element 21 generates the high-voltage strip image RH2 and the low-voltage strip image RL2.

Subsequently, a series of steps comprising: shifting the imaging location, controlling the collimator 9 based on the aperture, imaging the high-voltage strip image and imaging the low-voltage strip image is repeated relative to the respective areas R1-Rn. Specifically, referring to FIG. 11, the series of steps is repeated relative to the respective areas R1-Rn while the X-ray tube 5 is shifting from the imaging location indicated by the solid line and the imaging location indicated by the broken line. Consequently, the number n of the high-voltage strip images RH1-RHn and the number n of the low-voltage strip images RL1-RLn are generated. The data of the respective strip images are sent to the subtraction processing element 23.

Step S8 (Subtraction Step of a Strip Image)

The subtraction processing element 23 performs a subtraction processing using the respective receiving strip images. Specifically, the subtraction processing element 23 generates the subtraction image S1 having a strip-shape by performing the subtraction processing in which the image data of the low-voltage strip image RL1 are subtracted from the image data of the high-voltage strip image RH1. Referring the upper right of FIG. 12A, the subtraction image S1 is an image showing the X-ray image relative to the area F1. Specifically, relative to the area R1 having the width T in the x-direction, the range having the distance NL1 from the center line H in the y-direction and the distance NR1 from the center line H in the y-direction appears.

Specifically, the subtraction processing element 23 also generates the subtraction image S2-Sn having a strip-shape by performing the subtraction processing in which the image data of the low-voltage strip images RL2-RLn are subtracted from the image data of the high-voltage strip images RH2-RHn (middle figures and lower figures of FIG. 12A). The generated respective subtraction images S1-Sn are sent to the reconstruction element 25.

Step S9 (Reconstruction of a Mensurative X-Ray Image)

The reconstruction of the mensurative X-ray image is preformed following completion of the generation of the subtraction images S1-Sn. Specifically, the reconstruction element 25 connects the subtraction images S1-Sn in turn along the body axis direction of the subject M, so that a single mensurative X-ray image Q can be reconstructed. In such case, the locational (positional) alignment in the y-direction relative to the center line H as the baseline and each subtraction image is connected.

The mensurative X-ray image Q is an X-ray image that is necessary for the bone densitometry and showing the X-ray figure relative to the vertebra K and the proximity area of the vertebra, and of which the imaging range is controlled to be minimal. The reconstructed mensurative X-ray image Q is displayed on the monitor 37 and in addition, stored in the memory storing element 35. All steps relative to the X-ray imaging end when the mensurative X-ray image Q is obtained.

Effects of the Aspect of the Embodiment 1

According to the aspect of the Embodiment 1, when to take the X-ray image applied to a bone densitometry and so forth, the radiation dose against the subject can be controlled to be much lower. Hereinafter, the inventor sets forth the obtained effect due to the aspect of the Embodiment 1.

According to the X-ray imaging apparatus according to the aspect of the Embodiment 1, the vertebral area extraction element 27 extracts the vertebral area of the lumber vertebra in the X-ray image of the pre-image P. The correction level calculation element 29 calculates the correction level of the pre-image P based on the location of the extracted vertebral area. Specifically, the correction level is calculated as the distance from the center of the vertebral area (center Ko of the vertebra K of the third lumber vertebra) to the center Po of the pre-image.

And the imaging location of the pre-image is corrected based on the correction level and the pre-image P2 is corrected following the correction of the imaging location. In such case, relative to the pre-image P2, the center of the vertebral area coincides with the center of the pre-image, so that the respective vertebrae K can be located on the line of the center line H of the pre-image P2. And the imaging range of the mensurative X-ray image is set so that the center of the imaging range of the mensurative X-ray image can coincide with the center of the pre-image P2.

Accordingly, the imaging range of the mensurative X-ray image can be easily and accurately set by referring the pre-image P2 generated following the correction thereof. In addition, the center of the vertebral area coincides with the center of the imaging range of the mensurative X-ray image, so that the mensurative X-ray image Q can be an X-ray image suitable for observation of the vertebrae.

According to the conventional X-ray imaging apparatus, a pre-image is displayed on the monitor while the X-ray irradiation for fluoroscopy is being continued intermittently. And referring the displayed pre-image (video), the imaging location of the pre-image is corrected manually. In contrast, according to the aspect of the Embodiment, the calculation of the correction level and the correction of the imaging location can be automatically carried out following generation of the pre-image. Specifically, the pre-image is generated by irradiating the X-ray in a short period of the time corresponding to the single irradiation of the pulse X-ray, so that the imaging location can be automatically corrected using the displayed pre-image as a still image. Accordingly, when to obtain a pre-image at the adequate imaging location, the radiation dose against the subject can be controlled to be much lower.

In addition, the aperture calculation element 31 calculates the aperture of the respective areas of which the strip image is taken using the corrected pre-image relative to the imaging location. The aperture is calculated based on the minimal area required for bone densitometry. Accordingly, the X-ray image showing an X-ray image (figure) relative to the minimal area of the target area W, which is required for the bone densitometry can be obtained by reconstructing the strip image generated by irradiating an X-ray to the imaging range set based on the aperture. Specifically, when to image a mensurative X-ray image applied to bone densitometry X-ray image, the irradiation range of the X-ray can be controlled to be minimal. Consequently, when the mensurative X-ray image is taken, the radiation dose against the subject can be further suppressed.

In addition, the respective strip images applied to reconstruct the mensurative X-ray image are the subtraction images generated due to the difference between the X-ray image taken under a high tube voltage and the X-ray image taken under a low tube voltage. According to such subtraction image obtained by dual energy subtraction, the bone image and the soft tissue image, having a different X-ray transmittance each other, can be acquired individually. Accordingly, bone densitometry can be accomplished more preciously by using the mensurative X-ray image formed by the subtraction image.

Embodiment 2

Next, referring to FIGs., the inventor sets forth the Embodiment 2 of the present invention. The structure of the X-ray imaging apparatus 1A according to the aspect of the Embodiment 2 is the same as the Embodiment 1. However, the steps of operation related to the X-ray imaging apparatus according to the aspect of the Embodiment 2 are different from the aspect of the Embodiment 1 with regard to the point at which the Step S4 is skipped.

According to the aspect of the Embodiment 1, the respective imaging systems shift based on correction level following calculation of the correction level at the Step S3. And the pre-image 2 is newly taken following the correction of the imaging location (Step S4). And the aperture is calculated based on the distance between the center line H in the y-direction and the sideline SL relative to the pre-image P2 following the correction and so forth (Step S5). Following the calculation of the aperture, the location of the diaphragms 9a-9d are controlled based on the value of the aperture while shifting the imaging system to the imaging location of the strip image R1 (Step S6). Specifically, according to the aspect of the Embodiment 1, each imaging system shifts from the imaging location of the pre-image P to the imaging location of the strip image relative to the area R1 via the imaging location of the pre-image P2.

On the other hand, according to the aspect of the Embodiment 2, following calculation of the correction level at the step S1, the imaging range of the mensurative X-ray image Q is set without shifting the imaging system at the step S4. Specifically, the step of imaging the pre-image P2 by shifting the imaging system is skipped. And the aperture is calculated relative to the step S5 based on the appeared location of the vertebra in the pre-image P. Following the calculation of the aperture, the location of the diaphragms 9a-9d are controlled based on the value of the aperture while shifting the imaging system to the imaging location of the strip image P1. Specifically, according to the aspect of the Embodiment 2, each imagine system shifts from the imaging location of the pre-image P to the imaging location of the strip image relative to the area R1.

Hereinafter, the inventor sets forth the detail of the different point from the Embodiment 1 relative to the steps of operations of the X-ray imaging apparatus 1A according to the aspect of the Embodiment 2. In addition, the inventor skips to set forth the operations of the step S1 and the step S2 because such operations are the same as the Embodiment 1. In addition, as well as the aspect of the Embodiment 1, the length of the mensurative X-ray image 4 in the x-direction and the length of the pre-image in the x-direction are Px, and the length of the respective areas R1-Rn in the x-direction is T. In addition, it is given that the length Px of the mensurative X-ray image Q in the x-direction coincides with the length of the pre-image P in the x-direction.

Step S3 (Calculation of the Correction Level and Step S4 Setting of the Imaging Range)

At the step S3, the correction level calculation element 29 calculates the correction levels Dx and Dy using the pre-image P (referring to FIG. 13A) as well as the Embodiment 1. The image data of the pre-image P and the data of the correction level are sent to the imaging range setting element 30. At the step S4, the imaging range setting element 30 sets the location and the size of the imaging range (target area) of the mensurative X-ray image based on the correction level. Specifically, the central location of target area W is set so that the center of the vertebral center Ko can coincide with the center of the imaging range of the mensurative X-ray image.

In addition, the operator operates the input element 33 to input the data of the length T of the strip image in the x-direction and the data of the length Px of the tar et area W in the x-direction. The imaging range setting element 30 can set the imaging range of mensurative X-ray image Q based on the location of the center of the target area W and the length Px of the target area W in the x-direction. The imaging range setting element 30 sets the location of the strip-shaped areas R1-Rn, in which each strip image can be imaged, and the number of the areas (number of n) based on the imaging range of the mensurative X-ray image Q, the value of the length Px and the value of the length T. The calculated correction level, the image of the pre-image P on which the analytical processing is performed, the location of the target area W, and the location of areas R1-Rn are sent from the imaging range setting element 30 to the aperture calculation element 31.

Step S5 (Calculation of the Aperture)

The aperture calculation element 31 calculates the aperture relative to the step S5 using pre-image P. In such case, the aperture calculation element 31 detects the straight-line HD extending in the x-direction passim the center Ko of the vertebral area extracted from the pre-image P. And relative to the respective areas R1-Rn, the maximum distance K1 from the straight-line HD to the left sideline SL and the maximum distance KR from the straight-line HD to the right sideline SL are calculated respectively. In addition, the aperture calculation element 31 respectively calculates the apertures V1-Vn based on the K1, KR and the predetermined efficient $\alpha$.

Step S6 (Preparation For the X-Ray Imaging)

The preparation for the X-ray imaging according to the step S6 following the calculation of the aperture is carried out. The X-ray tube shifting element 13 and the FPD shifting element 15 respectively shifts the respective elements of the imaging system to the imaging location of the strip image relative to the area R1 based on the correction level Dx and Dy. Specifically, the X-ray tube shifting element 13 shifts the X-ray tube 5 by the distance of $(Px-T+2Dx)/2$ in the x-direction and by the distance Dy in the y-direction. The FPD shifting element 15 shifts the FPD 7 by the distance Dy in the y-direction.

The respective elements of the imaging system shift by Dy in the y-direction, so that the respective vertebrae K appearing on the location out of the center line H in the pre-image P are in-place on the line of the center line H of the respective strip images. And as set forth according to the aspect of the Embodiment 1, $(Px-T)/2$ is the distance from the imaging location of the pre-image P2 to the imaging location of the strip image of the area R1 in the x-direction, and Dx is the distance from the imaging location of the pre-image P to the imaging location of the pre-image P2 in the x-direction Accordingly, the X-ray tube 5 shifts by the distance $(Px-T+2Dx)/2$ in the x-direction while the respective elements of the imaging system are shifting in the x-direction, so that the respective elements of the imaging system shift directly from the imaging location of the pre-image P to the imaging location of the strip image relative to the area R1.

In addition, the collimator control element 17 controls an opening-and-closing shift of the diaphragms 9a-9d so that the X-ray irradiation field coincides with the range of the area F1 based on the aperture V1. Following shift of the X-ray imaging system and adjustment of the irradiation field of the X-ray, the preparation for X-ray imaging relative to the step S6 is completed. In addition, the later steps than the step S7 are the same as the Embodiment 1.

Effects of the Aspect of the Embodiment 2

According to the aspect of the Embodiment 1, the respective elements of the imaging system shift the imaging system from the imaging location of the pre-image P based on the correction level and generates the pre-image P2 by irradiating X-rays following the shift. And the aperture is calculated based on the vertebral area appearing in the pre-image P2. Subsequently, the imaging system shifts from the imaging location of the pre-image P2 to imaging location in the area R1 and the imaging of the strip image is performed.

On the other hand, according to the aspect of the Embodiment 2, the calculation of the correction level, the correction of the pre-image and the calculation of the aperture can be performed at the imaging location for the pre-image P before the correction. And the respective elements of the imaging system shift to the imaging location of the strip image while considering the correction level.

Therefore, according to the aspect of the Embodiment 2, the step of shifting the imaging system to the imaging location for the pre-image following the correction and the step of generating newly the pre-image by irradiating X-rays at the imaging location following the correction can be skipped. Accordingly, the time and the steps required for imaging the mensurative X-ray image can be cut further, so that an efficiency of X-ray imaging can be improved more.

The present invention is not limited to the aspect of the Embodiments set forth above and another alternative Embodiment can be implemented set forth below.

(1) According to the aspect of the Embodiment set forth above, the subtraction processing is performed following generation of the high-voltage X-ray image and the low-voltage X-ray image at each imaging location and the mensurative X-ray image is reconstructed by connecting the generated strip-shaped subtraction images. However, the step for acquiring the mensurative X-ray image is not limited thereto. Specifically, the reconstruction processing and the subtraction processing can be flipped in order.

In such case, the reconstruction element 25 is installed in the posterior of the image generation element 21 and the single high-voltage strip images RH can be reconstructed by connecting the strip-shaped high-voltage strip images RH1-RHn in the x-direction. In addition, the single low-voltage strip images RL can be reconstructed by connecting the strip-shaped low-voltage strip images RL1-RLn in the x-direction. The subtraction processing element 23 is installed in the posterior of the reconstruction element 25 and the mensurative X-ray image Q processed with the subtraction processing can be generated by getting the difference between the reconstructed high-voltage X-ray image RH and the reconstructed low-voltage X-ray image RL.

(2) According to the aspect of each Embodiment set forth above, an high-voltage and a low-voltage are alternately added to the X-ray tube 5 at each imaging location, so that the high-voltage strip image and the low-voltage strip image can be obtained in order. However, instead of such configuration, following acquiring the high-voltage strip images RH1-RHn relative to the areas R1-Rn, the low-voltage strip images RL1-RLn can be acquired relative to the areas R1-Rn.

(3) According to the aspect of each Embodiment set forth above, although it is given that the size of the imaging range of the mensurative X-ray image Q coincides with the imaging range of the pre-image, it is not necessary that the upper (or lower) edge of the mensurative X-ray image Q coincide with the upper (or lower) edge of the pre-image. In such case, referring to FIG. 8B, the imaging range of the X-ray imaging can be set by that the cursor C1 indicting the upper edge of the mensurative X-ray image Q and the cursor C2 indicting the lower edge of the mensurative X-ray image Q are superimposed to the pre-image on the display as needed, In such case, even if the imaging range of the pre-image P is set sufficiently as large, the imaging range of the mensurative X-ray image Q can be set in the just enough range for the bone densitometry. Therefore, the radiation dose on imaging the mensurative X-ray image can be controlled as much lower while facilitating to identify the target area W by enlarging the pre-image P.

(4) Referring to FIG. 11, according to the aspect of each Embodiment set forth above, the entire imaging range of the mensurative X-ray image is within the size of the FPD 7, so that the FPD 7 can be fixed to perform the X-ray imaging at the step S6. However, when the mensurative X-ray image relative to the long area is taken, the X-ray imaging can be performed while shifting the FPD 7 in the body axis direction of the subject M.

(5) When the correction level is calculated according to the aspect of each Embodiment set forth above, the pre-image of the same subject M acquired in the past can be referred. In such case, the correction level can be more accurately calculated referring the detail of the analytical processing of the pre-image performed previously.

(6) According to the aspect of the Embodiment 2 set forth above, one of the generation steps of the pre-image P2 is skipped without performing the correction of the imaging location at the step S4, but the location of the X-ray image appearing in the pre-image P can be corrected in the image data based on the correction level. In such case, referring to FIG. 14, a pre-image P2A is generated, in which the imaging location is virtually corrected. And the imaging range of the mensurative X-ray image Q and the respective ranges of the areas R1-Rn can be set based on the imaging range of the pre-image P2A. The operator can confirm the X-ray image appearing in the mensurative X-ray image and the imaging range of the mensurative X-ray image by referring the pre-image P2A.

(7) According to the aspect of each Embodiment set forth above, the mensurative X-ray image is generated by reconstructing the strip images, but the aspect of the present invention can be applied to acquire the mensurative X-ray image without generating-and-reconstructing the strip images. Specifically, an X-ray image applied to set the imaging area of the target area W of the subject (target area) to the imaging range is generated as the pre-image. In such case, the correction level is calculated based on the vertebral area extracted from the pre-image. And the imaging system shifts based on the correction level so that the center of the vertebral area coincides with the center of the imaging range of the target area. The X-ray image, of which the imaging range is the target area W at the location of the imaging system following the shift is imaged and the X-ray image generated by the image generation element 21 on such imaging, is applied as the mensurative X-ray image to the bone density analysis.

REFERENCE OF SIGNS

1 X-ray imaging apparatus
3 Tabletop
5 X-ray tube (X-ray source)
7 FPD (X-ray detection means)
9 Collimator
9a, 9b, 9c, 9d Diaphragm (Shielding element)
11 X-ray irradiation control element (Irradiation control means)
17 Collimator control element (Collimator control element)
21 Image generation element (Strip-image generation means, pre-image generation means)
23 Subtraction processing element (Subtraction processing means)
25 Reconstruction element (Reconstruction means)
26 Vertebral area extraction element (Feature region extraction means)
29 Correction level calculation element (Correction level calculation means)
30 Imaging range setting element
31 Aperture calculation element (Aperture calculation means)
33 Input element (Correction means
33a Pre-image generation directive switch (Pre-image generation directive means)
35 Memory (Memory storing means)
37 Monitor (Display means)
39 Main control element (Imaging system shifting control means)

It will be further understood by those of skill in the art that the apparatus and devices and the elements herein, without limitation, and including the sub components such as operational structures, circuits, communication pathways, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related X-Ray diagnostic devices, computer and operational controls and technologies of radiographic devices and all their sub components, including various circuits and combinations of circuits without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. Skilled artisans may implement the described functionality in varying ways for each particular application, but such implementation decisions should not be interpreted as causing a departure from the scope of the exemplary embodiments.

The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An X-ray imaging apparatus, comprising:
   an X-ray source that irradiates an X-ray to a subject;
   a detection means that detects the X-ray transmitted through said subject;
   an imaging system shifting means that shifts an imaging system relative to said subject and further comprises said X-ray source and said X-ray detection means;
   a strip image generation means that generates multiple strip images that are X-ray images having a strip shape along the body axis of said subject, by using a detection signal output from said X-ray detection means, and wherein a short direction of said strip is the body axis direction of said subject;
   a reconstruction means that reconstructs a single combined image by connecting said multiple strip images along the body axis direction of said subject, wherein said multiple strip images being generated by said strip image generation means;
   a pre-image generation means that generates an initial X-ray image as a pre-image that is applied to set an imaging range of said combined image by using a detection signal output from said X-ray detection means;
   a pre-image generation directive means that inputs a directive for generation of said pre-image;
   an irradiation control means that controls said X-ray source to make a single irradiation of a pulse X-ray from said X-ray source based on said directive input to said pre-image generation directive means;
   a feature area extraction means that extracts a feature area from the initial X-ray image appearing in said pre-image;
   a correction level calculation means that calculates a locational relationship between a center of said feature area extracted by said feature area extraction means and a center of said pre-image as a correction level; and
   an imaging system shifting control means that controls the imaging system shifting means so that the center of said feature coincides with the center of said combined image based on said correction level calculated by said correction level calculation mean.

2. The X-ray imaging apparatus, according to claim 1, wherein:
   said imaging system shifting control means controls said imaging system shifting means based on said correction level so that the center of said feature area coincides with the center of said imaging range of the pre-image; and
   said pre-image generation means regenerates said pre-image following control of said imaging system shifting means so that the center of said feature area coincides with the center of the imaging range of said pre-image.

3. The X-ray imaging apparatus, according to claim 1, wherein:
   said imaging system shift control means controls said imaging system shifting means so that the center of said feature area coincides with the center of the imaging range of said combined image, and additionally shifts said imaging system from the imaging location of said pre-image to the imaging location of said strip image.

4. The X-ray imaging apparatus, according to claim 1, further comprising:
   a collimator that controls an irradiation field of the X-ray irradiated from said X-ray source, wherein said collimator further comprises:
   a diaphragm that shields said X-ray;
   a collimator control means that controls an opening-and-closing and a shifting of said diaphragm during a use; and
   an aperture calculation element that calculates an aperture of said diaphragm as the aperture based on a width of said feature area extracted by said feature area extraction means when said respective strip images are generated; and
   wherein, said respective strip images are generated by said collimator control means controls said opening-and-closing and said shifting of said diaphragm based on said respective apertures.

5. The X-ray imaging apparatus, according to claim 4, wherein:
   said feature area extracted by said feature area extraction means is a vertebra area of said subject.

6. The X-ray imaging apparatus, according to claim 5, wherein:
   said aperture calculation means calculates said aperture relative to said respective strip images so that an area required for measurement of a bone density and said vertebral area are included in said X-ray irradiation field, and wherein a distance from said vertebral area is shorter than a predetermined value.

7. The X-ray imaging apparatus, according to claim 1, further comprising:

a subtraction processing means that performs a subtraction processing on said strip images generated by said strip image generation means when a high-voltage is added to said X-ray source and said strip image generated by said strip image generation means when a low-voltage is added to said X-ray source.

8. The X-ray imaging apparatus, according to claim 1, further comprising:

a subtraction processing means that performs a subtraction processing on said combined images reconstructed by said reconstructing means when a high-voltage is added to said X-ray source and said combined images reconstructed by said reconstructing means when a low-voltage is added to said X-ray source.

9. The X-ray imaging apparatus, according to claim 1, wherein:

said correction level calculation means calculates a correction level referring said pre-image previously generated relative to said subject.

10. The X-ray imaging apparatus, according to claim 1, further comprising:

a display means that displays said pre-image generated by said pre-image generation means;

a correction means that corrects a range of said extracted feature area relative to said pre-image displayed by said display means.

11. An X-ray imaging apparatus, comprising:

an X-ray source that irradiates an X-ray to a subject;

a detection means that detects the X-ray transmitted through the subject;

an imaging system shifting means that shifts an imaging system relative to said subject, and further comprising said X-ray source and said X-ray detection means;

a pre-image generation means that generates an initial X-ray image as a pre-image that is applied to set an imaging range of a target area of said subject using a detection signal output from said X-ray detection means;

a pre-image generation directive means that inputs a directive for generation of said pre-image;

an irradiation control means that controls said X-ray source to make a single irradiation of a pulse X-ray from said X-ray source based on said directive input to said pre-image generation directive means;

a feature area extraction means that extracts a feature area from said initial X-ray image appearing in said pre-image;

a correction level calculation means that calculates a locational relationship between a center of the feature area extracted by the feature area extraction means and a center of the pre-image as a correction level; and an imaging system shifting control means that controls said imaging system shifting means so that the center of said feature coincides with the center of said target area of said subject based on said correction level calculated by said correction level calculation mean.

* * * * *